United States Patent [19]

Cerchio

[11] Patent Number: 4,622,013
[45] Date of Patent: Nov. 11, 1986

[54] INTERACTIVE SOFTWARE TRAINING SYSTEM

[75] Inventor: Gerard J. Cerchio, San Jose, Calif.

[73] Assignee: Interactive Research Corporation, Santa Clara, Calif.

[21] Appl. No.: 612,760

[22] Filed: May 21, 1984

[51] Int. Cl.$^4$ .............................................. G09B 19/00
[52] U.S. Cl. ..................................... 434/118; 434/323
[58] Field of Search ........................ 434/118, 323, 335

[56] References Cited

U.S. PATENT DOCUMENTS 4,305,131 12/1981 Best ..................................... 434/323
4,360,345 11/1982 Hon ..................................... 434/323

Primary Examiner—Leo P. Picard
Attorney, Agent, or Firm—Flehr, Hohbach, Test, Albritton & Herbert

[57] ABSTRACT

An interactive training/expert computer system includes a computer subsystem for executing computer programs. A keyboard is used for entering data into the system, and a CRT displays the results of executing a computer program in the computer subsystem. A preselected computer program is resident in the computer subsystem. A tutor module interrupts the flow of data from the keyboard, interpreting and manipulating the input data, selectively generating messages in response to the input data, and selectively allowing a subset of the input data to be processed by the preselected computer program. The interpreting, manipulating, generating and allowing functions are dynamically determined in accordance with predefined criteria dependent on the contextual circumstances in the running of the preselected computer program.

24 Claims, 18 Drawing Figures

MONITOR FLOWCHART

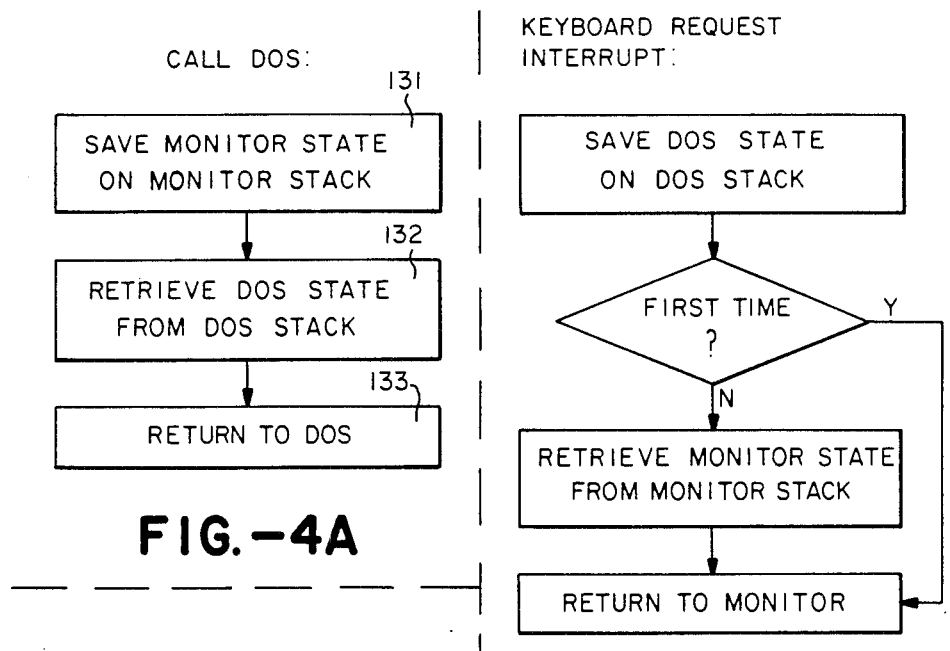
FIG.—4A
FIG.—4B
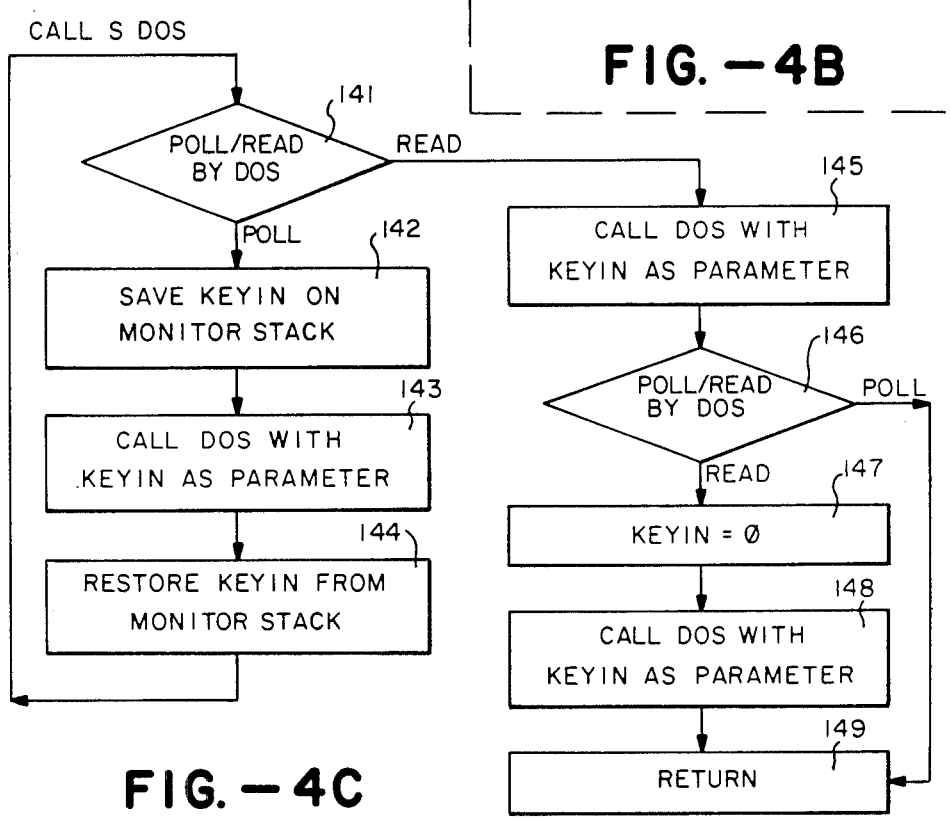
FIG.—4C

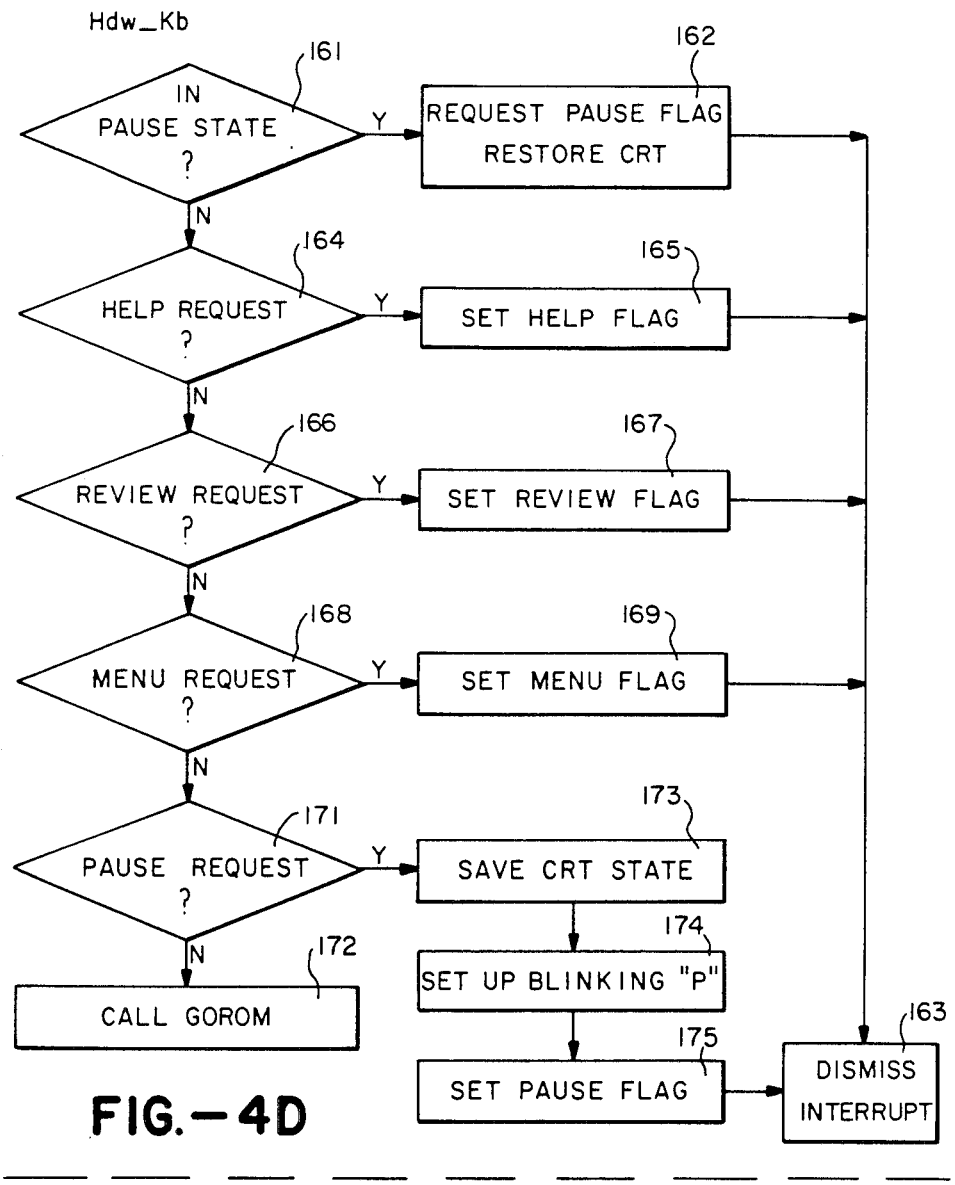
FIG.—4D
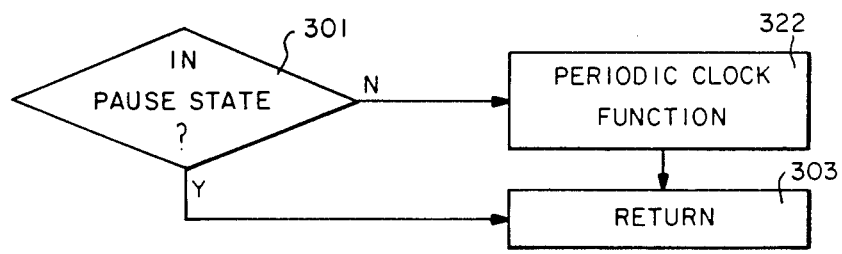
FIG.—4E

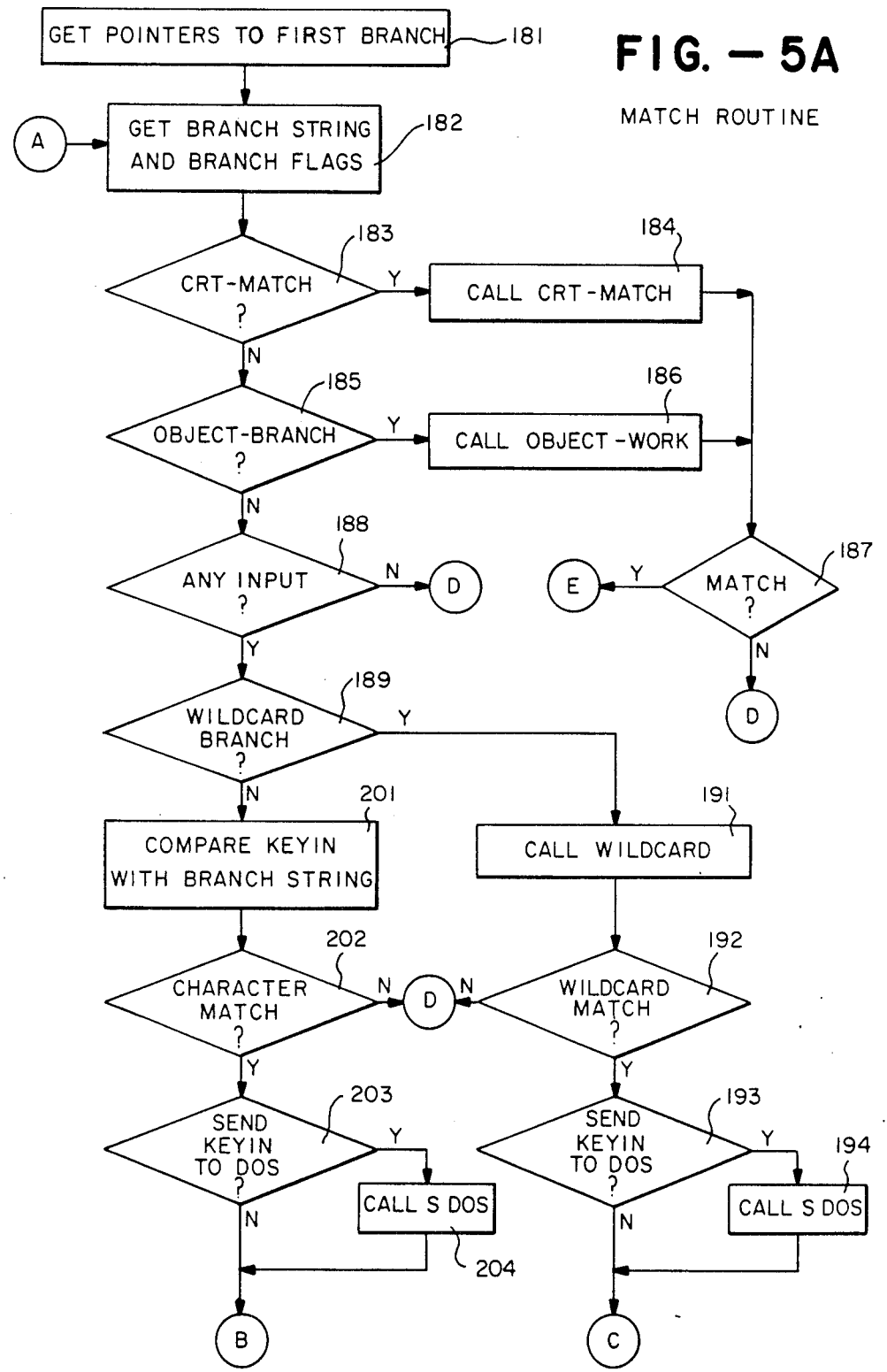
FIG.—5A
MATCH ROUTINE

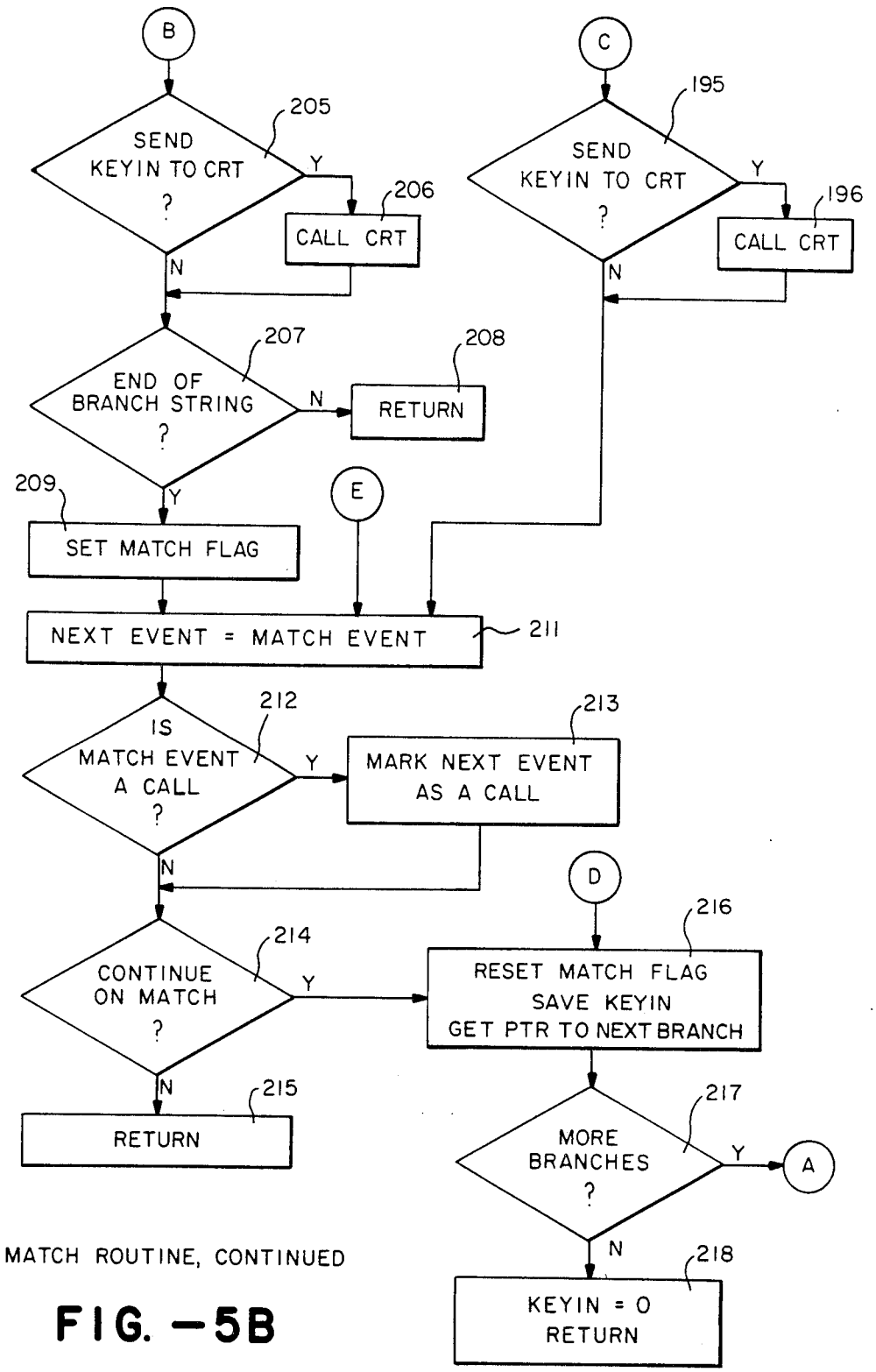
MATCH ROUTINE, CONTINUED
FIG. —5B

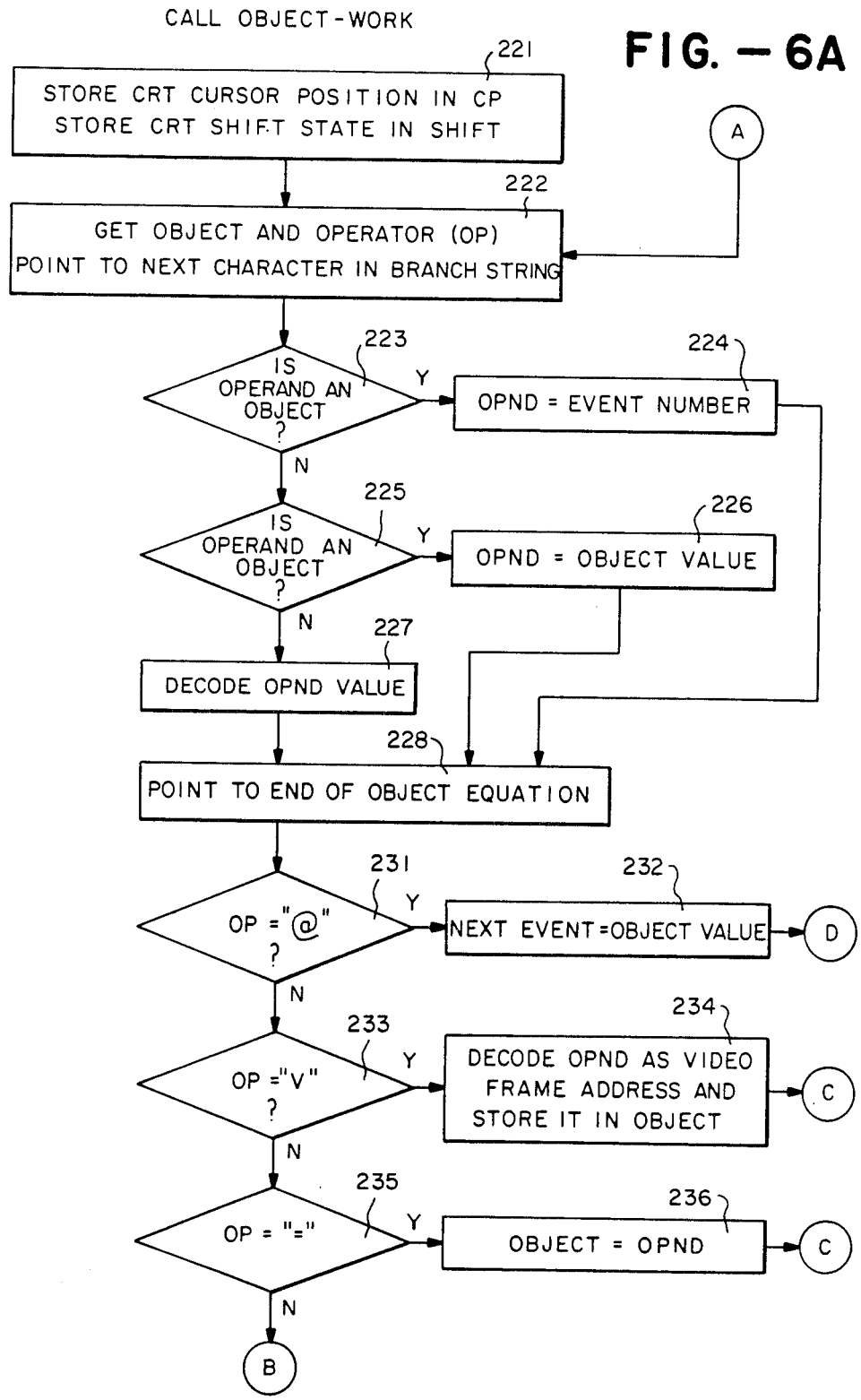
FIG. — 6A

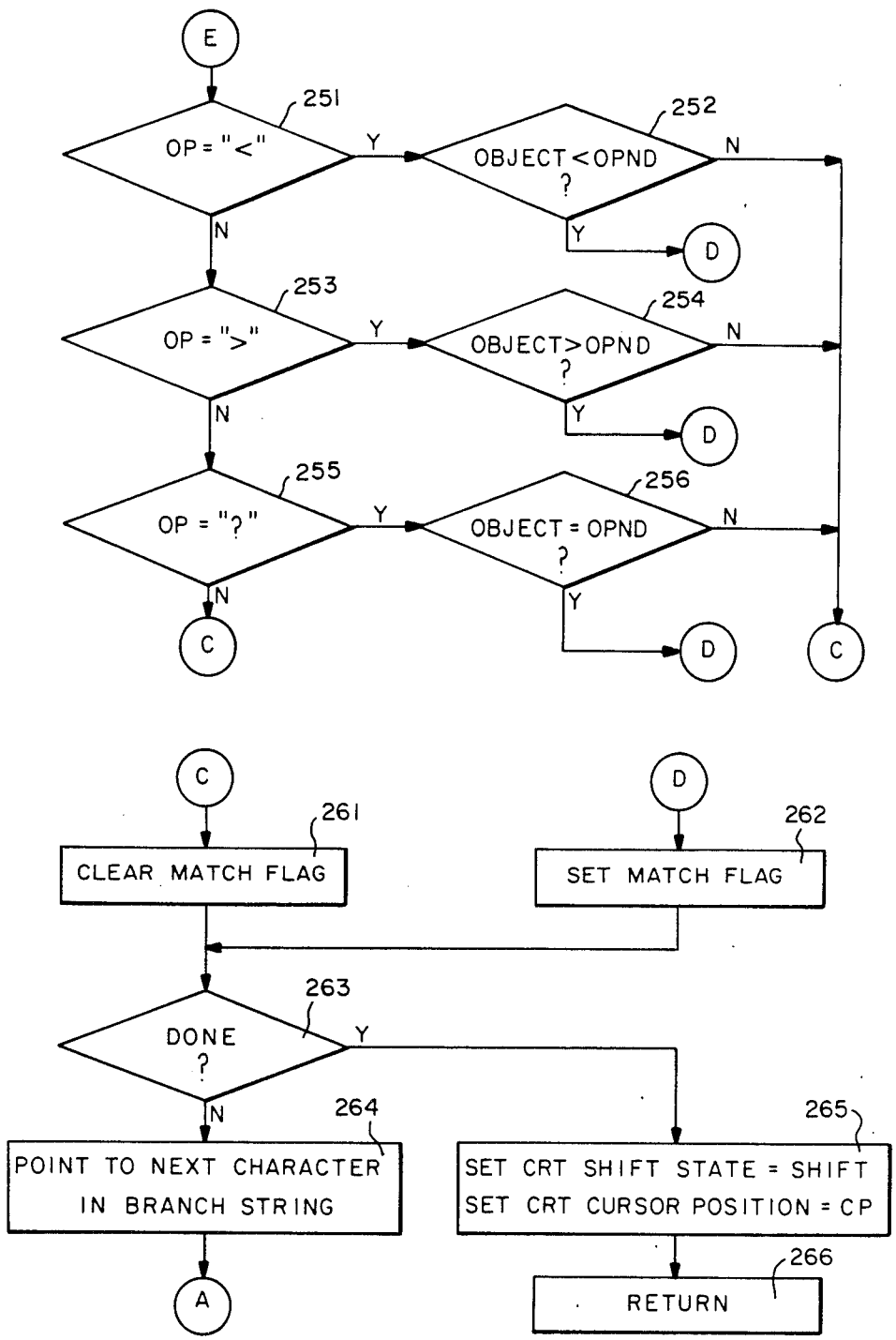
FIG. — 6c

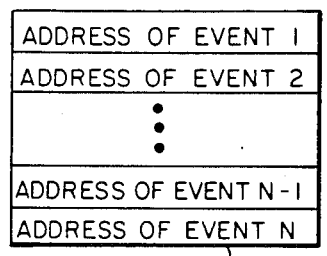
EVENT MAP
FIG. — 7A
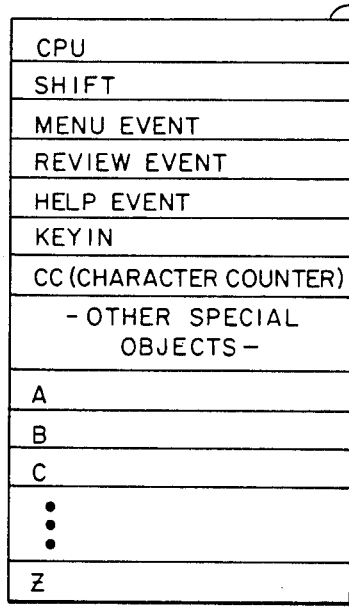
OBJECT TABLE
FIG. — 7B
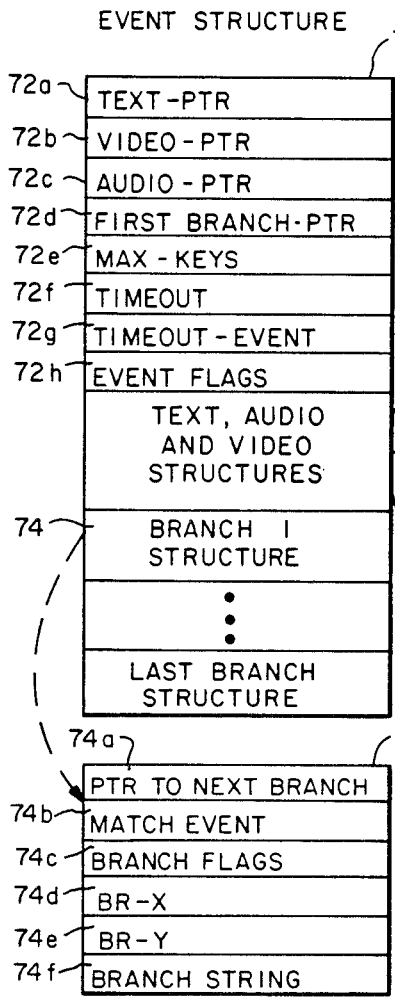
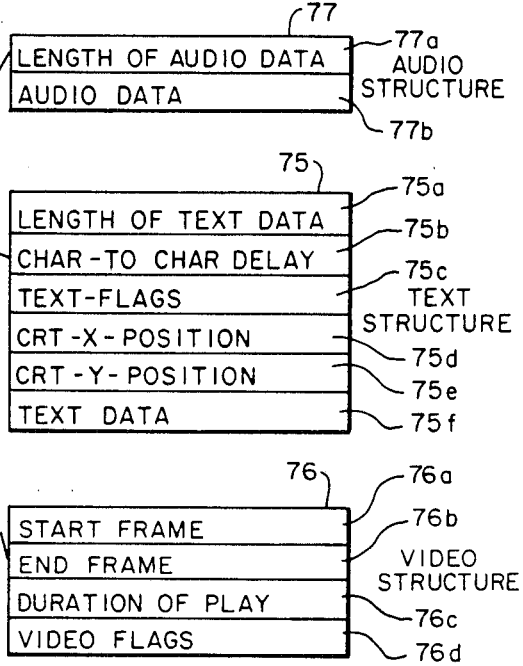
BRANCH STRUCTURE
FIG. — 7C

INTERACTIVE SOFTWARE TRAINING SYSTEM

This application pertains generally to a new computer system and in particular to a computer system which simulates a tutor for interactively training students to use selected computer programs. The system can also be used as an image-based expert or training system for tasks such as CAT-scan image analysis.

Prior art software training systems have included a variety of types of manuals and a variety of types of special computer programs designed to introduce the student to certain features of a selected computer program. Manual or text-based systems are totally unsatisfactory because (1) a large portion of potential users have neither the patience nor discipline to work through such a program; and (2) a manual cannot truly accommodate people with varied backgrounds and varying attention spans. Computer-based interactive software training systems are generally preferable to text-based because they require less discipline and patience on the part of the student. Such systems generally need to be complemented with a reference manual for use after the initial training is complete. The subject matter of the present invention concerns computer-based software training.

Computer-based (as opposed to text-based) prior art systems suffer at least two major deficiencies which are solved by the present invention: (1) they use a separate training program to introduce the student to certain features of the target or selected computer program instead of allowing the student to use the target computer program itself during the training; and (2) each training program must be written separately and specifically for a particular selected computer program, must duplicate many of the features of the selected computer program, and yet must be debugged just as carefully and thoroughly as any computer program.

A primary object of the present invention is to provide a system and method for training a student to use any selected computer program.

Another object of the invention is to allow the student to use the actual selected computer program while training.

Another object of the invention is to provide a system and method whereby the student is instructed on how through the use of a medium separate from the output medium used by the selected computer program or at least in such a way that the normal outputs created by the selected computer program are not disturbed.

Still another object of the invention is to provide a system for defining a training course for a selected computer program that requires neither simulation of the selected computer program nor the writing of a separate software training program for each selected computer program.

Yet another object of the invention is to provide a system suitable not only for interactive software training but also suitable for use as a display based training and expert system, wherein a video display, a picture quality display and an audio message system are used together, as necessary, to aid the user of the system.

In a preferred embodiment the present invention provides an interactive software training system for training a student to use a selected computer program. The system uses a computer or CPU (central processing unit) capable of executing the selected computer program. The system must have an input device (e.g., a keyboard or mouse) for accepting input data from the student, and a display device for displaying the results of executing the selected computer program. The flow of data into and out of the selected computer program can be monitored and interrupted.

A software interrupt module receives all the data entered through the input device. A monitor module interprets the input data and can also interpret the resulting output display on the display device generated by the selected computer program.

How the input and output data is interpreted and manipulated is defined by a courseware module. A separate courseware module must be authored for each selected computer program. Each courseware module includes a set of events associated with the selected computer program. Each event corresponds to one or more contextual circumstances in the operation of the selected computer program. An event can be used to perform certain tasks and to interpret input or output data.

Most events define one or more match values and a set of one or more tasks corresponding to each match value. A task is defined herein as a discrete operation, such as passing a datum from the monitor to the operating system, or setting a parameter to a particular value. A task is not used herein in the conventional sense of a process. Upon the receipt of data which matches a match value, a corresponding set of predefined tasks is performed. One type of task allows the data input by the student to be processed by the selected computer program. Another type of task defines which event is the next event to be used by the monitor. Match values associated with incorrect entries or entries which otherwise deviate from the planned training session can be blocked. The match values include both character-for-character match values and certain predefined wildcard match values. The tasks are selected from a defined set of available tasks. Through the use of these tasks, events can perform all, or practically all, functions performable by the computer system.

In a first preferred embodiment, explanational messages are generated using a speaker system and a second display device, preferably a laser disk display system. The use of both a second display system and an audio message system, while optional, allow the generation of a wide variety of explanational messages without interrupting the normal output generated by the selected computer program.

In a second preferred embodiment, the visual portion of the explanational messages is generated using one or more "windows" on the primary display device. This embodiment eliminates the need for a second display device, which may not be economically justified in certain circumstances.

Additional objects and features of the invention will be more readily apparent from the following detailed description and appended claims when taken in conjuction with the drawings, in which:

FIGS. 4A–4E are detailed flowcharts showing the co-processor aspect of the process of one embodiment of this invention.

FIGS. 5A-5B are detailed flowcharts showing the match routine part of the process of one embodiment of this invention.

FIGS. 6A-6C are detailed flowcharts showing the object interpreter aspect of the process of one embodiment of this invention.

FIGS. 7A-7C are detailed block diagrams of certain data structures used in one embodiment of this invention.

Figure 1:
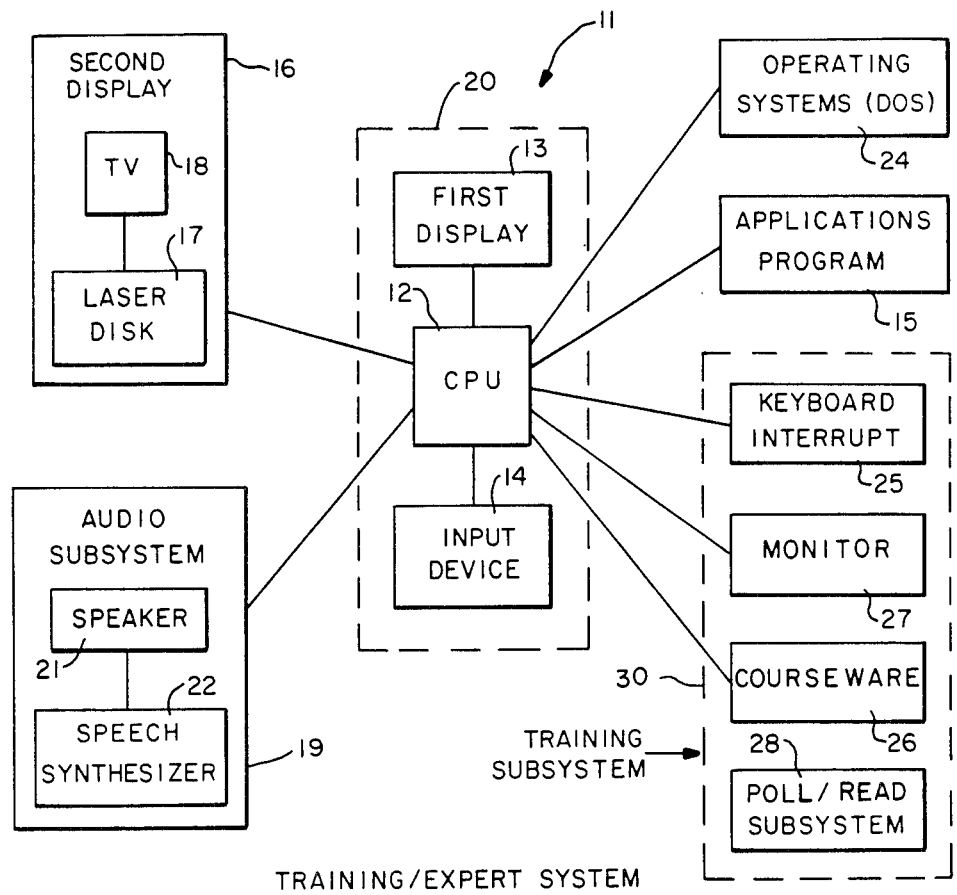
FIG. 1 is a block diagram of a system in accordance with the present invention.

Referring to FIG. 1, in a preferred embodiment of the invention the core of the system 11 is a standard computer subsystem 20, such as the IBM personal computer (also known as the IBM PC), including a CPU 12 (e.g., a microcomputer system, including a central processing unit, disk drive, etc.), a display device 13 (such as a standard CRT monitor), and an input device 14 (such as a keyboard or mouse). In most circumstances, the computer system 20 has an operating system 24 (also occasionally referred to herein as DOS) such as UNIX or DOS. The selected computer program 15 which the student is to be trained to use is usually an applications program such as a word processor program, a spreadsheet program or a data base program.

The selected computer program 15 can also be an operating system, such as UNIX or DOS, when the training course is a course on how to use the operating system. In such a case the selected computer program will generally also act as the system's operating system. (Note that while the operating system 24 and the target operating system 15 could theoretically be different, such an arrangement would normally be very cumbersome, except possibly in a main frame computer.) The selected computer program 15 will hereinafter be called the target or the applications program (even if it is the operating system 24). Naturally, the version of the applications program 15 to be used in the system 11 must be one designed to run with the particular computer subsystem 20 used in the system 11.

In the first preferred embodiment, the standard computer subsystem 20 is supplemented with a second display device 16, such as a laser disk 17 and television receiver 18 combination, and an audio device 19. It is generally intended that the second display device 16 be any system capable of producing high quality video images and video sequences, at least comparable in quality or resolution to standard U.S. television pictures. By way of contrast, the first display device 13 can be a standard CRT computer monitor capable of producing only black-and-white or only grey-scale images. In a second preferred embodiment, explanational messages are displayed by windowing the display on the first display device and confining the explanational messages to a portion of the screen that minimizes or avoids interference with the normal display produced by the target program.

The preferred embodiment also includes an audio device 19 comprising a speaker 21 and speech synthesizer system 22 which can be used to generate verbal messages in addition to those generated by the sound system (not shown) associated with the laser disk 17 and television 18 subsystem. It is often convenient in a training system to be able to generate verbal messages (such as short explanation to remind the trainee what to do next) without having to display a new image on the video display 16.

The training subsystem 30, which generally works as a co-routine, operating in parallel with the operating system 24, has four modules: a keyboard interrupt module 25 for receiving data from the input device 14 before it is processed by the operating system 24, a courseware module 26 for defining the training course, a monitor module 27 for interpreting input and output data and generally running the training system 11, and a keyboard request interrupt module 28 for transferring control to the monitor module upon the occurrence of a read or a poll of the keyboard. Polls and reads are usually performed by the operating system 24 when the applications program 15 is ready to receive more data. But any poll or read, even if executed by the applications program 15, will transfer control to the monitor module 27.

The explanation of how the system 11 can be used in interactive training and expert systems other than a software training system will be presented after the explanation of the structure and operation of the system 11 as an interactive software training system.

Figure 2:
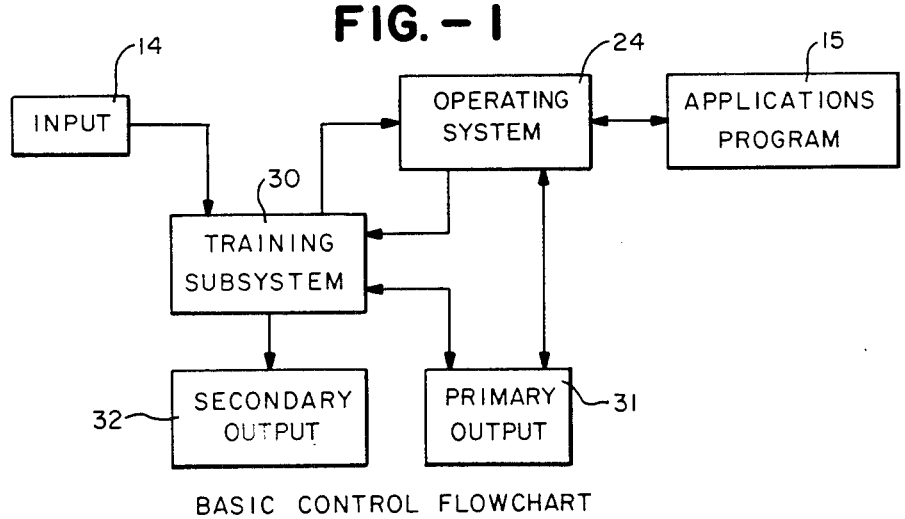
FIG. 2 is a general flowchart of the method used in the present invention.

Referring to FIG. 2, from a very simplistic viewpoint, the training subsystem 30 works by interrupting the flow of data from the input device 14 to the applications program 15 and interpreting the data entered into the system 11 before it is processed by either the operating system 24 or the applications program 15. This allows the training subsystem 30 a chance to act before unacceptable data is sent by the student to the applications program 15—and to decide if the student requires more instruction before proceeding with the next step in using the applications program 15.

The basic flow of control shown in FIG. 2 is different from the normal flow of control in most computer systems. Normally, the operating system 24 filters all data sent to the applications program 15 from input devices 14 and all data sent by the applications program 15 to output devices 31. In the present invention the connection between the operating system 24 and the input device 14 is rerouted through a training subsystem 30. In some circumstances, the flow of data from the operating system 24 to the output devices 31 is also rerouted through the training subsystem 30.

Still referring to FIG. 2, the training subsystem 30 works as a co-routine that operates in parallel with the operating system 24. The training subsystem 30 interprets input data and selectively sends data to the operating system 24 for processing by the operating system 24 and the applications program 15. When the operating system 24 tries to poll or read the input device 14 the training subsystem 30 answers the request. As part of the task of interpreting input data the training subsystem 30 controls a secondary output system 32, generally for communicating with the user of the system in a medium independent of that used by the operating system 24. The training subsystem 30 can also send output data directly to the primary output devices 31 (such as CRT monitors, printers, disks), completely bypassing the operating system 24.

The basic mechanics of setting up a co-routine such as the one used in the invention are as follows. The system's interrupt vectors for keyboard entries and keyboard poll/read requests are reset to point to entry points in the keyboard interrupt 25 and poll/read interrupt 28 modules, respectively. Thus whenever the student types on the keyboard 14 (i.e., enters data) the data is processed by the training subsystem 30 rather than by the operating system 24. Similarly, poll and read requests by the operating system 24 invoke the training subsystem 30 instead of the normal keyboard request software interrupt program (which is generally part of the basic input/output system of the CPU 12 or operating system 24).

When the training subsystem 30 is invoked by a keyboard request interrupt, the state of the operating system 24 is saved (in a stack associated with the operating system 24) and the training subsystem 30 is restored to control. When the training subsystem 30 is ready to transfer control back to the operating system 24 it saves the state of the training module (in a stack associated with the training subsystem 30), restores the operating system 24 to the state it occupied when it last performed a read or poll, and exits to the operating system 24 passing as a parameter the answer to the operating system's poll or read request.

Additionally, the training subsystem receives control on every "clock tick" of the computer system clock, by means of an interrupt vector. Any training subsystem operation may be initiated by the clock tick routine asynchronously of the student and the operation of the target. In the preferred embodiment, the clock ticks are counted, and if the total accumulated time exceeds a timeout parameter, the monitor 27 performs certain predefined tasks, as discussed below.

The particular method interrupting the flow of data from the input devices 14 to the target programs 15 is not essential to the invention in its broadest aspect. For instance, one advantage of using a keyboard interrupt module as described herein, but which is not essential to the invention, is that it allows the use of otherwise illegal key combinations (e.g., CNTRL ALT DEL) as function keys for special training subsystem functions.

While the preferred embodiment also contains the ability to interrupt and filter all output from the operating system, this facility need not be used in the design of many training systems incorporating the invention. The ability to interrupt and filter output can be used, for instance, to avoid overwriting a valuable file, or to direct output to a different file than the output would normally go to, or to modify output sent to the first display device 13 in some useful way.

Also, even though the preferred embodiment described herein assumes that data is entered on a keyboard, the invention applies equally well to systems with other types of data input. The basic flow of control between the training subsystem 30 and the operating system 24 remains the same. Only the particular courseware 26 (as explained below) used with the invention is dependent on the nature of the input data received.

Referring to FIGS. 7A–7C, the courseware 26 comprises a special set of data structures which defines how the training interprets input data. The three basic data structures used by the training subsystem are an event map 71, event structures 72, and an object table 73. The main other data structures used in the system are standaard stack data structures, including a DOS stack, a monitor stack, an event stack. The use of each data structure is described below.

Events and Branches

The most basic data structure is called an event 72. Only one event is used at any one time by the monitor module 27 to interpet input data. Events specify how data is to be interpreted in a few ways. Generally, each event corresponds to one or more contextual circumstances in the operation of the training program. For instance one event may be used when the student needs to enter the command "print", another event may be used when the student has forgotten to press the return key after entering data, and another event may be used when the student has made so many mistakes that he apparently has not absorbed the portion of the training course already presented.

The contextual circumstances of the training course are evaluated by the system with four categories of tests: (1) match branches, which compare entered data with a predetermined match string; (2) screen-match branches, which compare output data from the target program with a predetermined screen-match string; (3) object branches, which manipulate and test certain system-defined and certain user-defined variables called objects; and (4) timeout tests, which detect failure of the student to make a correct entry (or for the system to respond to the student's commands in a specified way) within a specified timeout period.

For each type of tests there is a corresponding data structure or set of data structures. For convenience, the name of the test and the name of the corresponding data structures are the same. There are three distinct types of branch data structures: match branches, screen match branches, and object branches. The timeout data structure 72f is merely a single integer parameter within the event data structure 72.

In the preferred embodiment, all branch structures have the same general format shown in FIG. 7C. The type of any particular branch is determined by the settings of the branch flags 74c in its branch structure 74, as explained below. For each type of branch structure the branch string 74f has a distinct function. In other embodiments different data structures could be used for each type of branch without affecting the substance of the invention described herein.

Referring now to FIG. 7C, a typical event structure 72 includes a plurality of branches. Note that any particular event structure can have any number of branches, including zero or one branches. When there are a plurality of branches, the branches are sequentially organized by means of a singly linked list of the sort well known to those skilled in the art. The branches are sequentially tested by the training subsystem 30, using a pointer 74a in each branch structure 74 to find the next branch.

Match Branches

The first type of test, called a match branch, provides a match value (generally, a string of one or more characters) and a set of corresponding tasks to be performed when the input data matches the match value. In the preferred embodiment each such match value and corresponding set of tasks are collectively called a branch 74. A match branch, has a match value, called a branch string 74f, a set of flags 74c indicating what to do upon the occurrence of a match, and a match event 74b specifying what event to invoke upon the occurrence of a match.

Referring to FIG. 7A, in the preferred embodiment the match event value is not a pointer directly to the match event but rather an index to an event map 71 holding pointers to all the events defined by the courseware 26. Thus events are indirectly addressed through the event map 71. Since events are variable length data structures and can be located quite far from one another in the memory array of a large courseware module 26, indirect addressing through an event map makes generation of the courseware module easier, as will be understood by those skilled in the art.

TABLE 1A

Seq: 002 name: BG001L05 # 00001 Com: begin intro
Video Starting Frame: 210 Video Ending Frame 2920
Video Duration: 1644
Video Mode of Play is: Play Channel 1
Text data length: 7 Row: 1 Column: 79
Character delay 0
---* TEXT *---
"CNTRL P"
---* End *---
Clear CRT
* BRANCH 1 *
Match Event: BG002L05
---* Branch Text *---
PIP
---* End Text *---
Allow KB to DOS
** BRANCH 2 *
Match Event: BG046L04
---* Branch Text *---
PRINT
---* End Text *---
Allow KB to DOS Ignore case
* BRANCH 3 *
Match Event: BG003L05
---* Branch Text *---
\**
---* End Text *---
Single wild character
Maximum Key presses: 6
Time out: 90 seconds
Time out event: BR005L15

TABLE 1B

Seq: 040 name: BG010L05 # 00001 Com: get format
Video Starting Frame: 34008 Video Ending Frame: 0
Video Duration: 0
Video Mode of Play is: Single Frame
* BRANCH 1 *
Match Event: BG020L05
---* Branch Text *---
c
---* End Text *---
Ignore case
* BRANCH 2 *
Match Event: BG046L35
---* Branch Text *---
Format b:
---* End Text *---
Allow KB to DOS Ignore case
* BRANCH 3 *
Match Event: BR045L05
---* Branch Text *---
E+1;KEYIN&255;KEYIN[32
---* End Text *---
Object operation
* BRANCH 4 *
Match Event: NULL
---* Branch Text *---
X=E;X+1
---* End Text *---
Object operation
* BRANCH 5 *
Match Event: BR400L05 Column: 1 Row: 1
---* Branch Text *---
EOF
---* End Text *---
* BRANCH 6 *
Match Event: BG440L05
---* Branch Text *---
\**
---* End Text *---
Single wild character
Maximum Key presses: 9
Time out: 90 seconds
Time out event: BR006L15

TABLE 1C

Seq: 045 name: BG010L10 # 00001 Com: delete error
Video Starting Frame: 34122 Video Ending Frame: 0
Video Duration: 0
Video Mode of Play is: Single Frame
* BRANCH 1 *
Match Event: 0
---* Branch Text *---
"CNTRL H"
---* End Text *---
Allow KB to DOS Continue on Match
* BRANCH 2 *
Match Event: BG046L55 Column: 1 Row: 23
---* Branch Text *---
COPY X:
---* End Text *---
Maximum Key presses: 7
Time out: 90 seconds
Time out event: BR006L25

Tables 1A, 1B, and 1C contain representational views of three typical event structures 72. These representational views are useful in describing the event structure 72. Referring now to Table 1A, which shows a fairly simple event, the operation of match branches is explained. Each time a datum is entered it is compared with the match string 74f in each branch of the event until it finds a sub-match. A sub-match occurs when all the characters entered so far (i.e., since the character counter was last reset) match the corresponding portion of the match string. Thus in the example shown in Table 1A, if the user typed in the letters "p", "r", and "i", the first letter (i.e., "p") would cause a sub-match with branch 1, the second letter (i.e., "r") would cause a sub-match with branch 2, and the third letter (i.e., "i") would also cause a sub-match with branch 2.

A "match" does not occur until the input data fully matches a whole match string. Note that all match strings are branch strings but, as will be explained below, not all branch strings are match strings. The system 11 puts no constraints on the the length of the match strings specified in the courseware; a match string can be whatever length is required by the context of the event.

Each time a datum is entered by the student, the monitor 27 sequentially compares the input data with each of the match strings in the branches of the current event. Upon the occurrence of the first match or sub-match the comparison process stops, with one exception explained below.

To understand what happens upon the occurrence of a match or a sub-match, the purpose each branch flag must be understood. In the preferred embodiment there are eight branch flags 74c. See Table 2. Each is a single-bit value, and the eight flags are stored collectively in a single byte in the branch data structure 74.

Note that each branch structure has its own set of flags. The type of the branch is determined by the BR_CRT_M and the BR_OBJECT flags. If neither flag is on (i.e., enabled) then the branch is a match branch. If the BR_CRT$_{13}$M flag is on then the branch is a screen-match branch. If the the BR$_{13}$OBJECT flag is on then the branch is an object branch. Clearly the BR$_{13}$CRT$_{13}$M and BR$_{13}$OBJECT flags are mutually exclusive: at most one can be enabled in any branch structure.

TABLE 2

| BRANCH FLAG | BRANCH FLAGS DESCRIPTION |
|---|---|
| BR_CALL | Match event begins an event subroutine |
| BR_DOS | Send input data to DOS upon sub-match |
| BR_CRT_M | This is a screen-match branch |
| BR_CRT | Send input data to CRT |
| BR_PASS | Match on a single wildcard |
| BR_OBJECT | This is an object branch |
| BR_NOCASE | Ignore case of input data when checking for a match |
| BR_NOBR | Do not branch upon occurrence of a match |

Only match branches can let input data pass through to the operating system 24. Each input data is sent to the operating system (DOS) 24 upon the occurrence of a sub-match with the match string in a match branch if the branch's BR_DOS flag is on. If there is no sub-match or if the BR_DOS flag is off, the operating system 24 does not receive the input data. Thus if the student makes an entry that does not match any branch string with an enabled BR_DOS flag in the current event, the entry will not affect the state of the applications program 15 (i.e., it will be as if the entry had never been made). On the other hand, an "incorrect" entry by the student can be handled in several different ways.

First the "incorrect" entry may match a catch-all wildcard branch (e.g., Branch 3 in Table 1A) which (1) transfers control to another event that causes the generation of an explanational message by the training subsystem 30, and (2) does not allow the datum to be passed to the target program 15 (i.e., with the BR_DOS flag of the wildcard branch being not enabled). In a second example, an "incorrect" entry could match a branch which (1) allows the datum to be passed to the target program 15, and (2) transfers control to another event that explains how to correct the "incorrect" entry. Thus different types of "incorrect" entries can be handled in distinct ways by the training subsystem 30.

When the student makes a "correct" entry (i.e., an entry that matches a branch string in the current event) the data can be passed to the applications program 15 via the operating system 24. On the other hand, the author of the courseware 26 can prevent the entered data from being sent to the applications package until a full match is achieved by sending the entered data only to the CRT monitor upon the occurrence of each sub-match, and then using another event to send the full text of the correct entry to the operating system upon the occurrence of a match. This would be done by setting up a first event with a branch having a match string equal to the correct entry, an enabled BR_CRT flag, a disabled BR_DOS flag, and a match event that contains an appropriate initial text task for sending the full text of the correct entry to the operating system 24. The enabled BR_CRT flag causes the monitor 27 to echo the entered data on the first display device 13 at the current position of the display's cursor, but does not cause the entered data to be passed to the operating system 14. Note that in some contexts it may be appropriate for a branch to have both an enabled BR—CRT flag and an enable BR_DOS flag.

Upon the occurrence of a match, the event indicated by the match event 74b will be invoked unless: (1) the BR_NOBR flag is enabled, or (2) the match event 74b has a value of NULL (e.g., zero in the preferred embodiment). If the BR_NOBR flag is enabled, the monitor 27 continues to test the other branches in the event, if any. Note that normally the monitor 27 stops checking for a match when the first match or sub-match occurs. If the match event is the NULL event, the current event remains in effect even after the occurrence of a match.

A typical event having a branch with the BR_NOBR flag enabled is shown in Table 1C. In this example, the student has made an "incorrect" entry and has been told to backspace (denoted "CNTRL H" in Branch 1) until the input line looks like "COPY X:". Thus the backspaces by the student are let through to DOS, but the monitor continues on to test Branch 2, which looks at the input line. The monitor cyclically tests Branches 1 and 2 until Branch 2 is satisfied or a timeout occurs.

A set of one or more events can be used as an event subroutine that is used in one or more contexts in the operation of a training course. To call a set of events as an event subroutine the branch making the call specifies the first event in the event subroutine as the match event and has the BR_CALL flag enabled. When the event subroutine returns, the event invoked is the next event after the calling event. That is, the event to be returned to is the next event referenced in the event map 71 after the calling event. (Optionally, in other embodiments, the calling event data structure could specify the event to be invoked after the subroutine returns.) To execute a return from an event subroutine, a branch in the subroutine must specify a match event equal to the RETURN event, which is equal to −1 in the preferred embodiment.

The two flags not yet discussed, BR_PASS and BR_NOCASE, both relates to details of the process of determining if input data matches a specified match string. The BR_NOCASE flag indicates that, if enabled, the case of the input characters should be ignore when comparing it to the match string. Thus uppercase input characters can match lowercase match string characters and vice versa.

The BR_PASS flag, if enabled, indicates that the match string is a special wildcard character. Each wildcard character matches a set of two or more input data values. Using wildcard characters enables the author of the courseware to reduce the number of branches and events required to determine if an input datum fits within a certain class of input values. The wildcard characters used in the preferred embodiment are shown in Table 3.

The "\*" in each wildcard string is merely a marker used to indicate that the following letter specifies a wildcard set. In a preferred embodiment any match string can have embedded wildcards. Thus the match string "FL\*N" would match the input data strings FL0, FL1, . . . FL9. In the embodiment shown in the program listings at the end of this specification, wildcards can be used only as a single character match string in a match branch. Such match branches are designated by enabling the BR_PASS flag therein.

TABLE 3

| WILDCARD MATCH VALUES | |
|---|---|
| Wildcard String | Match Value Set |
| \** | any input character |
| \*x (x=0 to 9) | any key denoting x |
| \*A | any cursor control key |
| \*F | all function keys |

TABLE 3-continued

| WILDCARD MATCH VALUES | |
|---|---|
| Wildcard String | Match Value Set |
| \*L | all letters |
| \*N | all numbers |
| \*P | all key pad keys |
| \*R | return key |

Screen-Match Branches

Screen-match tests are similar to match tests, except that the string to be compared with the screen-match string 74f is on the CRT monitor 13 of the core computer subsystem 20. The BR-X and BR-Y parameters 74d and 74e of the branch structure 74 specify the column and row on the CRT monitor 13 of the first letter of the screen string. The branch string 74f of the screen-match branch 74 is called the screen-match string. The length of the screen string to be compared with the screen-match string is the length of the screen-match string 74f. If, when the screen-match test is performed, the designated screen match string matches the screen string, then the monitor 27 will generally invoke the match event. As with match branches, if the BR__CALL flag is set then the match event will be called as an event subroutine. Similarly, if the BR__NOBR flag is set then the monitor will continue to test the other branches in the current event instead of invoking the match event, but such a use of the BR__NOBR flag with a screen-match branch is unlikely to be of any practical use. More useful, if the match event is the NULL event, the screen match can be used to prevent the testing of the succeeding branches of the event until the the screen string no longer matches the screen-match string 74f (e.g., until the student enters data or a command which causes the target program 15 to alter the data displayed on the primary display device 13).

In the preferred embodiment the BR__PASS, BR__NOCASE, BR__DOS, and BR__CRT flags are inoperative in screen-match branches. In other embodiments, however, it would straightforward to be able to selectively ignore the case of the screen string (although the author of the courseware should practically always know the case of the screen string which is indicative of a correct action by the student) and to allow the use of wildcards in the screen-match string 74f.

Object Branches

Object branches can perform a number of functions including mathematical operations and tests, heuristic tests, moving the CRT monitor's cursor, and changing the shift state of the keyboard. The branch string 74f of an object branch contains one or more object "equations". Each object equation either performs an operation on an "object" or performs a test of the value of an "object". In the preferred embodiment, the set of available types of object equations is as shown in Table 4.

TABLE 4

| OBJECT OPERATIONS | |
|---|---|
| TYPE EQUATION | DESCRIPTION |
| mathematical: | |
| OBJ=NNNN | set object to NNNN |
| OBJ+NNNN | add NNNN to OBJ |
| OBJ−NNNN | subtract NNNN from OBJ |
| OBJ*NNNN | multiply OBJ by NNNN |
| OBJ/NNNN | divide OBJ by NNNN |
| logical: | |
| OBJ&NNNN | AND NNNN with OBJ |
| OBJ! | COMPLEMENT OBJ |
| OBJ\|NNNN | OR NNNN with OBJ |
| branch: | |
| OBJ@ | branch to event(OBJ) |
| OBJ<NNNN | branch if OBJ is less than NNNN |
| OBJ>NNNN | branch if OBJ is greater than NNNN |
| OBJ?NNNN | branch if OBJ equals NNNN |
| video: | |
| OBJV | display video frame(OBJ) |
| OBJVNNNN | display video frame NNNN |

In these "equations" the first parameter (OBJ) is called the object, the second parameter is called the operator, and the third parameter (NNNN), if any, is called the operand. The operand can be either a number, another object, a event number, or a video frame member.

"Objects" are basically variables whose value can be tested or changed mathematically or logically. The result of mathematical and logical object operations is stored in the object referenced in the equation. The branch operations cause a branch to the match event if the branch test is satisfied, except that if the "@" operator is used when the value of the object (i.e., the value of OBJ) is used as the match event value. The video operations cause the secondary display 16 to display a particular video frame.

Objects can have different types of values: simple numerical values, match event values (which are essentially an index pointer for the event map 71), and video frame values. In the preferred embodiment, each type of value is not encoded in any special way. It is the responsibility of the courseware author to ensure that the literal value of the object or the operand (i.e., NNNN) is meaningful in the context it is being used. Furthermore, in the preferred embodiment objects are 16-bit (i.e., two-byte) integers.

In the preferred embodiment there are two types of objects: dedicated objects having a specific system function, and general variable objects. In the preferred embodiment general variable objects are like normal variables in a computer program and can be given any value without inadvertently affecting another part of the system. The set of dedicated objects in the preferred embodiment is shown in Table 5.

TABLE 5

| DEDICATED OBJECTS | | |
|---|---|---|
| OBJECT NAME | LISTING NAME | DESCRIPTION |
| CP | X | Cursor Position on the CRT monitor: first bytes is the column (Y) position; last byte is the row (X) position |
| SHIFT | C | Shift state of the keyboard |
| MENU | B | Event to be invoked when the user enters Menu interrupt: (CNTRL) (ALT) (DEL) on keyboard |
| REVIEW | T | Event to be invoked when the user enters Review interrupt: (CNTRL) (TAB) on keyboard |
| HELP | Q | Event to be invoked when the user enters Help interrupt: |

TABLE 5-continued

DEDICATED OBJECTS

| OBJECT NAME | LISTING NAME | DESCRIPTION |
|---|---|---|
| | | (CNTRL) (SHIFT) on keyboard |
| KEYIN | K | Next keystroke, if any, to be interpreted |
| CC | E | Character Counter: the position in the match-string of the character to be compared with KEYIN |

In the preferred embodiment, as shown in FIG. 7B, the letters A through Z are available as general variable objects and all the dedicated objects have distinct names from the general variables. In the embodiment shown in the program listings at the end of the specification, the letters listed under the heading "LISTING NAME" are reserved for use as dedicated objects. Only the remaining 19 letters are available for use as general variable objects. As will be clear to those skilled in the art, these restrictions on the names of the objects are arbitrary and unrelated to the subject matter of the invention. In other embodiments the number of distinct general variable objects and the names of the general variable objects can be unrestricted, except that they must not duplicate the names of the dedicated objects.

Object branches can serve many useful purposes. For instance a general variable object can be used to count the number of mistakes the user has made in a particular portion of the training course. When that object's value exceeds a particular predetermined value the system can branch to a special review section of events to help the student learn material that he apparently missed the first time through. The KEYIN object can be tested to determine if the input falls within a class of input values other than those provided by the wildcard values. The cursor position object can be reset to a new value so that the student can enter data at the correct location on the CRT monitor 13 without knowing how to get there. The character counter can be reset before the student starts entering a new string or can be decremented in order to give the student a second chance to make a correct entry without having to restart at the beginning of the string.

The MENU, REVIEW, and HELP objects hold special event values which the student can invoke at any time by typing in the proper key sequence. See Table 5 describing the dedicated objects. This allows the student to interrupt the training session if he doesn't understand something (by invoking the HELP event), wants to go through a portion of the training session a second time (by invoking the REVIEW event), or wants to switch to a different portion of the training course (by invoking the MENU event).

Non-Branch Event Tasks

Events perform several functions in addition to those specified by means of branches. In order to facilitate the discussion of these tasks, reference is now made to Table 6 which describes the event flags 72h.

Timeout

In the preferred embodiment, if the none of the branches in an event cause a branch to a new event within a specified period of time, called the timeout period, then then a specified timeout event is automatically invoked. The timeout period is specified by parameter 72f in the event structure 72 and the timeout event is specified by parameter 72g in the event structure 72. If the timeout period for an event is zero, then the event branches are not tested unless the EXEC_OBJ flag is enabled, as explained below. If the timeout event is the NULL event, the next event after the current event in the event map is invoked.

Initial Tasks

When an event is invoked it can perform up to three initial tasks before it executes any branches. The three types of initial tasks are TEXT, VIDEO, and AUDIO. The order in which these initial tasks is to be performed is specified by relative numerical values of the pointers 72a, 72b and 72c to the corresponding TEXT data structure 75, VIDEO data structure 76, and AUDIO data structure 77. (I.e, the task corresponding to the lowest value pointer is executed first.) The TEXT task can send a specified string to the operation system 24, or to the CRT monitor 13, or to some other output device such as a printer. The VIDEO task generates a video frame or video sequence on the secondary display device 16. The AUDIO task generates a specified message on the supplementary audio system 19.

TABLE 6

| EVENT FLAGS | |
|---|---|
| EVENT FLAG | DESCRIPTION |
| CLEAR_KBD | Clear keyboard buffer when event is invoked |
| EXEC_OBJ | Execute screen-match and object branches before testing for timeout |
| CLR_STACK | Clear the event subroutine stack when event is invoked |
| CRT_LOOP | Continue to execute screen-match and object branches even when no keyboard input has been received |
| KEEP_C_COUNT | Do not zero the character counter when the event is invoked |

Text Tasks

The text data structure 75 is shown in FIG. 7C. The length of the text string 75f is specified by parameter 75a. If the target program 15 is known to be able to absorb data at a particular rate, the rate at which the text string characters are sent to the operating system 24 can be controlled by setting the character-to-character delay parameter 75b to an appropriate value (in milliseconds). The text flags 75c, shown in Table 7, specify the destination of the text string.

TABLE 7

| TEXT FLAGS | |
|---|---|
| TEXT FLAG | DESCRIPTION |
| TXT_CRT | Send the text string to the CRT |
| TXT_PRT | Send the text string to the printer |
| TXT_DOS | Send the text string to DOS |
| TXT_WT | If Set, respond to polls by sending back the NULL character; If not Set, respond to polls by sending the next character in the text string |

If the TXT_CRT flag is set the text string is to be sent to the CRT monitor 13 at the column and row specified by the CRT_X and CRT_Y parameters 75d and 75e. If the TXT_PRT flag is set then the text string 75f is sent to the system's printer (or an equivalent output device, not shown in FIG. 1). Finally, if the TXT_DOS flag is set the text string is sent to the operating system 24. The manner in which text is sent to the operating system 24 is determined by the TXT_WT flag. The purpose of the TXT_WT flag is to handle applications programs that indiscriminately read in data even if doing so overflows the program's keyboard input buffer. If the TXT_WT flag is not set, polls by the operating system 24 are answered by sending it the next character (i.e., by sending it a signal indicating that another keyboard character has been received). If the TXT_WT flag is set, polls by the operating system 24 are answered by sending it the NULL character (i.e., by sending it a signal indicating that no keyboard character has been received).

Video Tasks

The video data structure 76 is shown in FIG. 7C. In the first preferred embodiment, video tasks can display a single video frame, a sequence of single video frames, or motion picture sequence. The video tasks can also have an associated sound track that plays on one or two audio channels. These capabilities of the preferred embodiment are tied to the capabilities of an industry standard laser disk player, but the particular set of video capabilities is not essential to the invention. What is important is that (in this first preferred embodiment) there be a second display device, in addition to the one associated with the core computer system 20, that is capable of producing relatively high quality images (e.g., the quality of standard U.S. television pictures) suitable for a training course or for displaying the images needed in the particular expert system (e.g., a CAT-scan image analysis system) with which the invention is being used.

The video tasks work generally by sending signals to the laser disk player which specify the frame or frames to be played, or the starting and ending frames of a motion picture sequence. The video data structure 76 includes a start-frame parameter 76a and an end-frame parameter 76b which reference particular video frames on a laser disk. Clearly, in the first preferred embodiment each courseware module 26 for a particular training course must have an associated laser disk or equivalent set of video images. In many cases a single laser disk will be able to hold the images for several training courses. In any case, the events in the courseware 26 must reference the video frames to be played with those events. In the preferred embodiment there is no facility for indirectly referencing the video images through an index table on the laser disk. Therefore the courseware will generally be tied to a particular video disk. But in future embodiments including such a video frame index table, the start- and end-frame parameters 76a and 76b could be indirect pointers and the video disk could be changed or upgraded without having to rewrite the video data structures 76 in the courseware 26.

TABLE 8

| VIDEO FLAGS | |
|---|---|
| VIDEO FLAG | DESCRIPTION |
| VID_STEP_FORE | Display next single video frame |
| VID_STEP_BACK | Display next prior video frame |
| VID_SEQ | Display a sequence of single video frames, each for a period of V_TIME milliseconds |
| VID_PLAY | Display a motion picture sequence |
| VID_SINGLE | Display a single video frame |
| VID_LEFT | Turn on the left audio channel |
| VID_RIGHT | Turn on the right audio channel |
| VID_PAUSE | Blank the video screen |

TABLE 8-continued

| VIDEO FLAGS | |
|---|---|
| VIDEO FLAG | DESCRIPTION |
| VID_RESET | Reset the video player |

The video flags, shown in Table 8, specify the type of the video sequence to be played and which audio channels, if any, are to be used with the video sequence, among other things.

The video data structure has seven mutually exclusive flags which determine the mode of video operation. If the VID_SINGLE flag is set the video frame referenced by the Start-Frame parameter 76a is displayed. If the VID_STEP_FORE flag is set the video player 17 steps forward one frame and displays that frame. If the VID_STEP_BACK flag is set the video player steps back one frame and displays that frame. IF the VID_SEQ flag is set the video player sequentially displays each video frame from Start-Frame 76a to End-Frame 76b for V_TIME 76c milliseconds. If the VID_PLAY flag is set the video player displays a motion picture sequence starting at Start-Frame 76a and ending at End-Frame 76b. If the VID_PAUSE flag is set then the video screen 18 is blanked. Finally, if the VID_RESET flag is set the video player 17 is reset. The video player is generally reset only once at the beginning of the training course.

The VID_RIGHT and VID_LEFT flags are used only in video play mode (i.e., when VID_PLAY is set). They determine whether the right and left audio channels of the video player are to be turned on or off. Also in video play mode the V_TIME parameter 76c is used to determine how long to wait after the motion picture sequence is initiated before allowing the monitor to perform its next task. For instance, a text task could be performed while a video sequence is being watched by the student.

In the second preferred embodiment, wherein only a single display device is used, video tasks define one or more windows and the video data to be displayed therein. As in the first preferred embodiment, the courseware can cause the display of a single image, a sequence of images or even an animated sequence. In an exemplary embodiment using two windows, a first window could be used to display an explanational message and a second window could be used to highlight the portion of the "normal" display associated with target program which the student should be concentrating on. The position of these windows is context dependent, with the first (explanational) window being position so as be least intrusive on the "normal" display. Also the monitor could leave the "normal" display unencumbered by windows except when the monitor 27 needs to communicate with the student. Since the use of windows is well known in the prior art, those skilled in the art will be able to apply the teachings of the first preferred embodiment to build embodiments using a single windowed display.

Audio Tasks

The audio data structure 77 is shown in FIG. 7C. In the preferred embodiment the audio system 22 is a speech synthesizer (e.g., the TMS 5220 made by Texas Instruments) that plays encoded speech messages. The speech is encoded using standard LPC encoding techniques well known in the art. The audio message is generated by sending the encoded audio data 77b to the speech synthesizer 22 which translates the audio data into electrical signals that drive a speaker 21. The length of the audio is specified by the length parameter 77a in the audio data structure 77.

Method

Figure 3A:
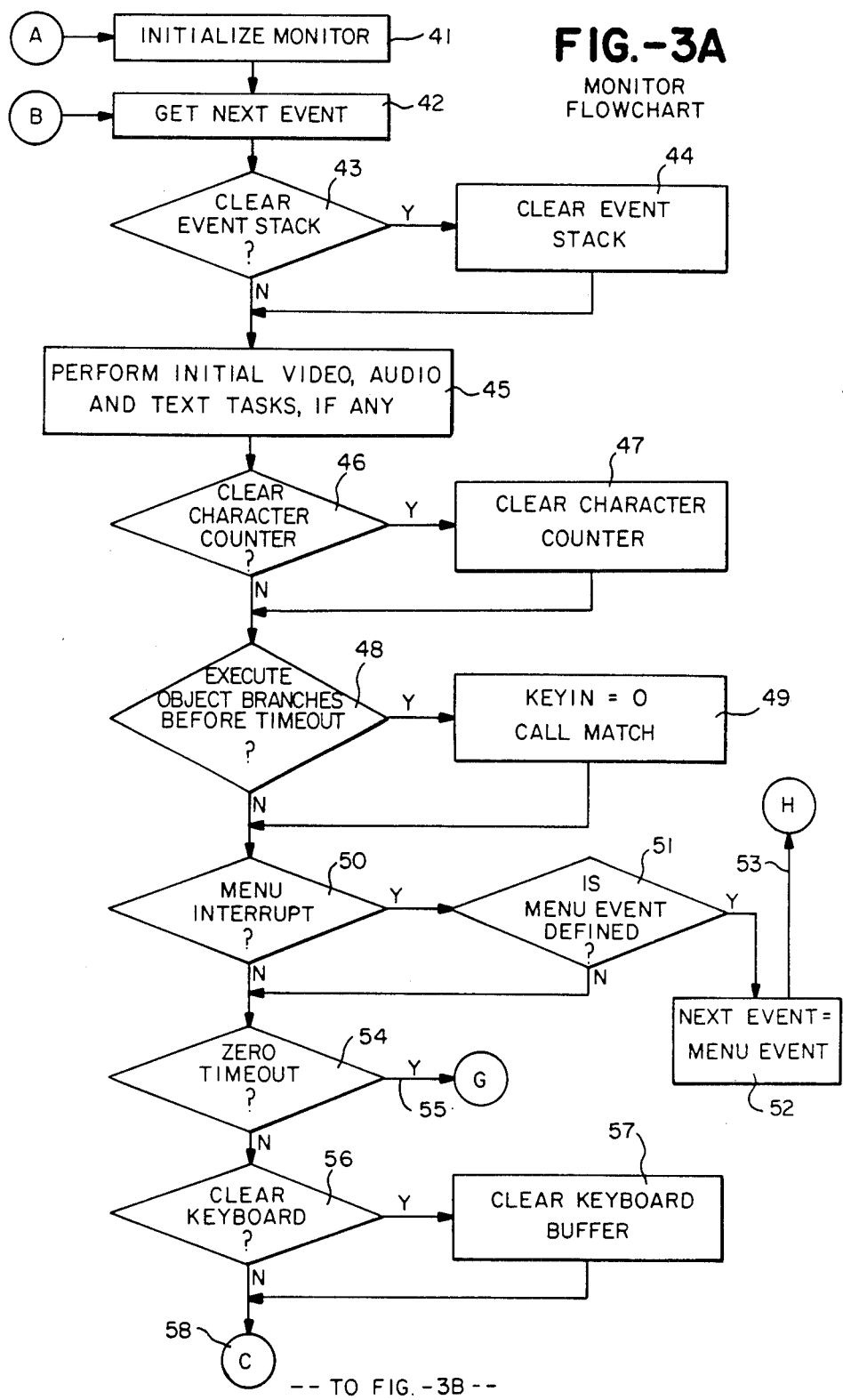
FIGS. 3A–3C are detailed flowcharts of an exemplary computer process, herein called a monitor routine, employing the method used in the invention.
Figure 3B:
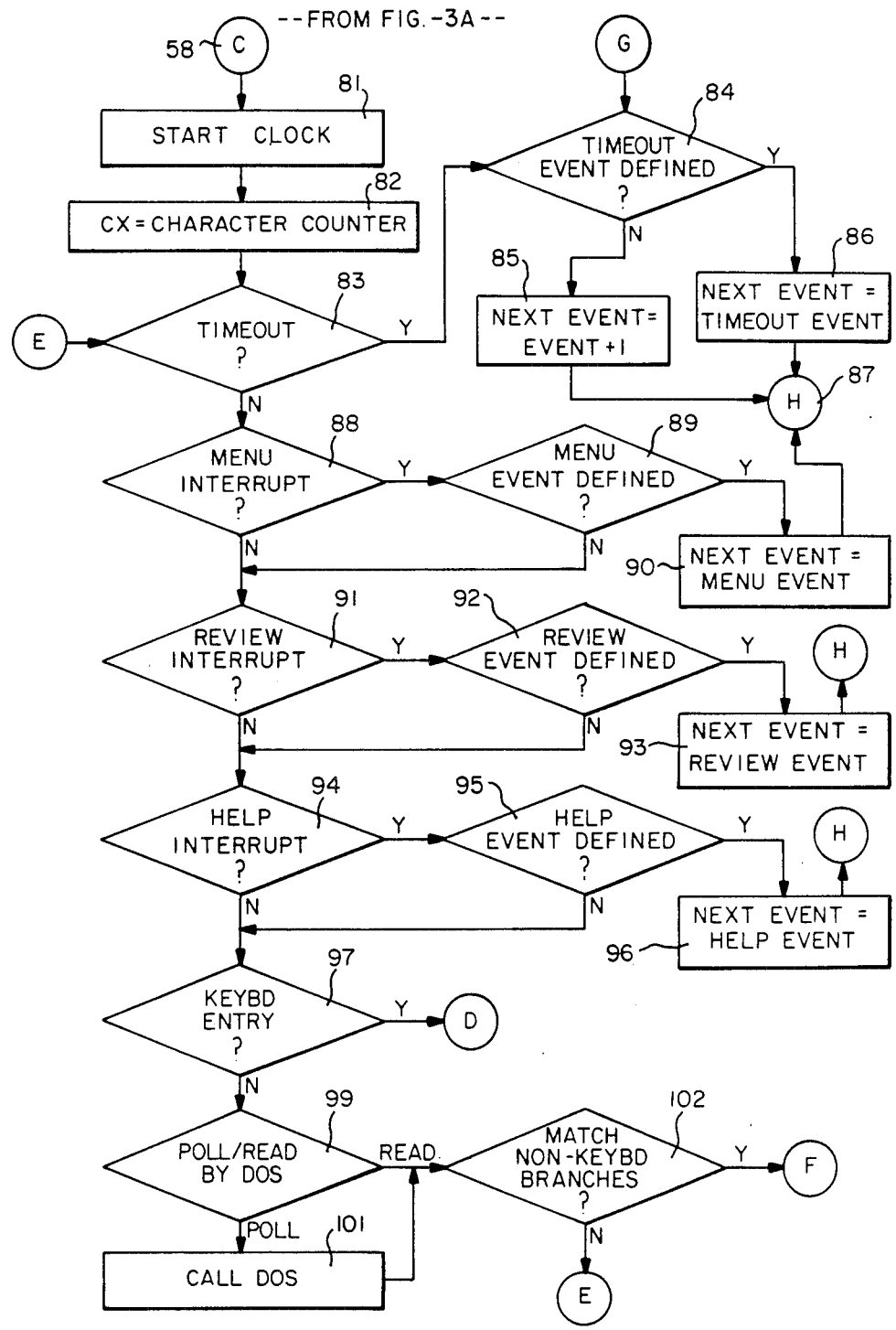
Figure 3C:
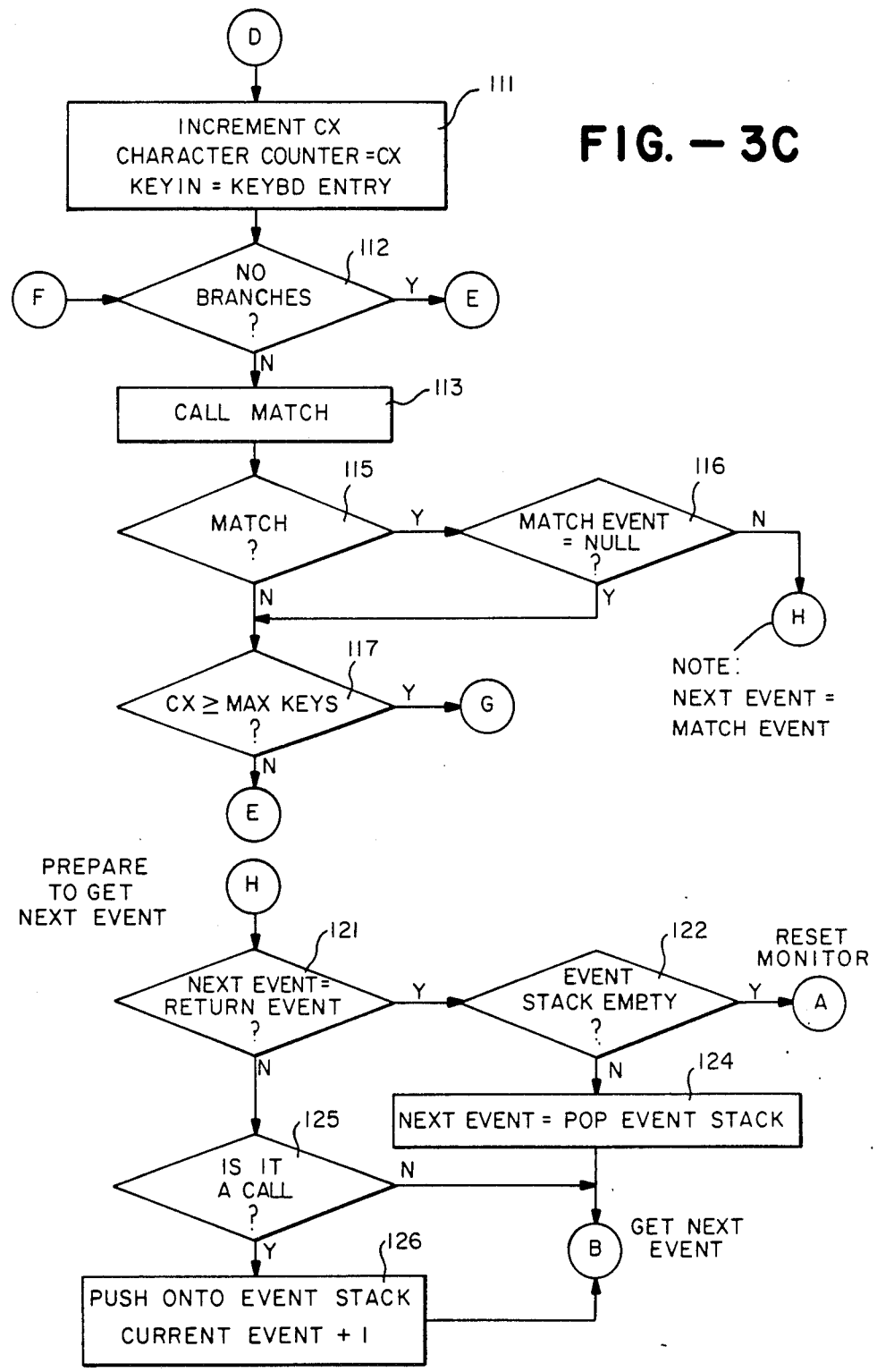

The method of the invention as performed in the preferred embodiment is shown in the flowcharts of FIGS. 3A-3C, 4A-4D, 5A-5B, 6A-6C. Note that the entry points (denoted in the figures as a capital letter enclosed in a circle) for each set of figures (e.g., FIGS. 3A-3C) comprises a distinct set (i.e., entry point A in FIGS. 3A-3C is distinct from entry point A in FIGS. 5A-5B).

Main Monitor Process

The flowchart of FIGS. 3A-3C corresponds to the MAIN program in the program listings. The monitor 27 is initialized at 41 by loading the courseware 26 into the computer 20 memory. This involves loading the event map, the object table, and the events into appropriate portions of memory; setting up stack pointers for the monitor stack and event stack; setting the event pointer to the first event in the courseware 26; and various other tasks well known to those skilled in the art of designing assembly language system programs. Block 41 is re-executed only if the monitor 27 needs to be totally reset, for example if the monitor encounters a situation (e.g., a set of data entries from the student) that unexpectedly causes a return from an event subroutine but the event stack is empty.

The main event loop begins at block 42, where certain parameters from the current event are loaded into temporary registers. The first test 43 in the event loop tests the CLR_STACK flag (see Table 6) in the event structure. If it is set, the event stack is cleared at block 44. In most embodiments this merely involves resetting the event stack pointer to the bottom of the stack. The event stack is generally reset only by the events at the beginning of each section of the training course. These are the events which are invoked when the student interrupts the training sequence by with either a Menu interrupt (which invokes the event pointed to by the MENU object) or a Review interrupt (which invokes the event pointed to by the REVIEW object).

The initial Text, Video and Audio tasks, if any, are performed next at block 45. The order of these initial events is indicated by the sort order of the numerical values of the pointers 72b, 72c and 72d of the corresponding data structures. For a description of these initial tasks see the above descriptions of the corresponding data structures.

At block 46 the KEEP_C_COUNT flag (see Table 6) in the event structure 72 is tested to see if the character counter used in match branch tests should be reset at block 47. The character counter is reset by most events which include match branches corresponding to correct student data entries; it is not reset by many events which are designed to allow the student to recover from a mistaken data entry.

At block 48 the EXEC_OBJ flag (see Table 6) in the event structure 72 is tested to see if the non-match (i.e., the screen match and the object) branches should be tested at this point. If the EXEC_OBJ flag is set, then the match routine, described below with reference to FIGS. 5A-5B, is called at 49. The KEYIN parameter for the match routine is set to the NULL character at 49 so that, as explained below, the match branches are not tested.

At block 50 the keyboard input buffer is checked to see if the student has requested a Menu interrupt. See Table 5. If so the MENU object is tested at 51 to determine if the menu event is "defined" (i.e., if the MENU object is not equal to NULL). If the menu event is defined the next event pointer is set to the menu event, at block 52, and the process jumps to entry point H to block 121, described below.

The Timeout parameter 72f is tested at 54. If it is zero none of the branches will be tested and the process jumps to entry point G at block 84, where the pointer to the next event is set.

Block 56 begins the preparations for the timeout loop, which starts at entry point E (block 83). The CLEAR_KBD flag (see Table 6) in the event structure 72 is tested to see if the keyboard buffer should be cleared. If so all unprocessed data entries from the student are deleted at block 56 and the student restarts will a clean slate.

The timeout clock is started at block 81 and character counter is copied into the CX register at block 82.

At block 83, which is the beginning of the timeout loop, the timeout clock is tested to determine if the elapsed time since the timeout clock was last started exceeds the length of time specified by the timeout parameter 72f. Timeout generally occurs if the student fails to make a correct entry in the allotted time, but can be used for other purposes. If the timeout event is defined (i.e., not equal to the NULL event), as determined at block 84, the next event pointer is set to the timeout event 72g (block 86); otherwise the next event pointer is set to point to event after the current event (block 85). In either case the process then continues at entry point H.

If timeout has not yet occurred, the keyboard buffer is checked to see if the student has entered a Menu interrupt (block 88), Review interrupt (91), or Help interrupt (block 94). If any such interrupt has been entered, the corresponding MENU, REVIEW or HELP object is tested to see if it is defined (block 89, 92 or 95, respectively) and, if so, the next-event pointer is set equal to the corresponding object (block 90, 93 or 96, respectively). If the object is not defined the process continue to check for any of the other interrupts and moves onto block 97 where the keyboard buffer is tested to see if any data entries have been made by the student. This test for a keyboard entry is not performed by a normal poll or read of the keyboard because that would cause a software interrupt, as explained below. Rather, the monitor directly tests a special register set by the keyboard input interrupt routine when input is received.

In an keyboard entry is found, the process jumps to entry point D to block 111 (FIG. 3C) where the process will test the branches, if any, in the event. If no keyboard entry is found, the type of keyboard request interrupt used by the operating system (DOS) 24 (which passed control to the training subsystem) is tested at 99. If DOS 24 was polling the keyboard (i.e., merely checking to see if any data was entered) DOS 24 is called at 101. This gives DOS 24 some CPU cycles, which it may need for proper operation. When DOS 24 performs another read or poll control will return to the monitor process at the point where the monitor called DOS 24. In other words, when DOS 24 performs another read or poll control will pass to block 102. If DOS 24 was reading the keyboard, DOS 24 is not called. Instead control is passed to block 102.

At block 102 the CRT_LOOP flag (see Table 6) is tested to determine if the object branches and screen match branches of the event should be tested even though no keyboard input has been received. If the CRT_LOOP flag is not set then the process resumes at entry point E to block 83 at the beginning of the timeout loop. If CRT_LOOP flag is set then the process jumps to entry point F to block 112 (FIG. 3C).

Referring now to FIG. 3C, if a keyboard entry was found, the monitor process picks up at entry point D to block 111 where, in preparation for calling the Match routine, the keyboard entry is placed in the KEYIN object and the Character Counter and the corresponding CX register are incremented. The CX register is used to determine the position of the keyboard entry in the input string which is being compared with match strings in match branches.

At block 112 the process checks that the event has at least one branch. Note than an event may have only initial tasks and no branches; an event may even have no initial tasks and no branches, although such an event will generally not be particularly useful. Also note that if block 112 is entered through entry point F then KEYIN is equal to NULL because no keyboard entry was received by the system. If there are no branches (i.e., if first-branch pointer 72d is equal to zero) then the process resumes at entry point E to block 83 at the beginning of the timeout loop.

If there is at least one branch in the event then the Match routine is called at block 113. The flowchart for the Match routine is shown in FIGS. 5A and 5B.

If the Match routine found a "match" that means that the test specified by a branch caused the match flag to be set. As will be explained in more detail below, the match flag is set if a match branch finds an input string that matches the full length of the match string; if a screen match finds a string at the specified screen location that matches the screen-match string; or if any object branch test is satisfied. Also, when there is a match, the next event pointer is set to the match event specified in the branch structure.

If the match event is the NULL event (see block 116) then the timeout loop continues at block 117. At block 117 the CX register (which is generally equal to the character counter unless an object branch changed it when the Match routine was called) is compared with the Max-Keys parameter 72e in the event structure 72. If CX exceeds Max-Keys it usually means that the student has entered more keystrokes than is reasonable under the circumstances. If so, the process invokes the timeout event (if one is defined) by proceeding to block 84 (see FIG. 3B) via entry point G. If CX does not exceed Max-Keys the process resumes at entry point E to block 83 at the beginning of the timeout loop.

If the match event is not the NULL event the process continues at entry point H to block 121, where preparations are made to invoke the next event.

At block 121 the next event pointer is tested to determine if it equals the RETURN event (which is equal to −1 in the preferred embodiment). If the next event is the RETURN event then the pointer to the next event is obtained by popping the pointer from the event stack. Generally, the RETURN event is invoked only at the end of an event subroutine. However it is possible for any branch to specify the RETURN event as the match event, although this is generally not good courseware programming practice because the results may be vary depending on the context in which the branch is tested. Thus if the next event is the RETURN event the process continues at block 122 where the event stack is tested to see if it is empty. Clearly the event stack should not be empty if a RETURN event is called for. But if this does happen the monitor is reset by restarting the monitor process at entry point A to block 41. The courseware can deliberately use this capability by invoking the RETURN event in order to reset the monitor process, for instance when no input has been received from the student for several minutes and it is presumed that the student has abandoned the training session.

If the next event is the RETURN event and the event stack is not empty, the pointer to the next event is popped from the event stack at block 124 and the process resumes at entry point B to block 42 (see FIG. 3A) at the beginning of the event loop.

If the next event is not the RETURN event the BR_CALL flag (see Table 2) (i.e., the BR_CALL flag of the branch which caused the "match" to occur) is tested at block 125. If the BR_CALL flag is not set, the process resumes at entry point B to block 42 (see FIG. 3A) at the beginning of the event loop. If the BR_CALL flag is set then the pointer to the event after the current event is pushed onto the event stack at block 126. Then the process resumes at entry point B to block 42 (see FIG. 3A) at the beginning of the event loop.

Co-processor Routines

Referring to FIGS. 4A–4D, the subprocesses of the co-processor aspect of the invention are: the DOS subroutine (FIG. 4A), the SDOS subroutine (FIG. 4C), the keyboard request interrupt routine (FIG. 4B), the keyboard interrupt routine (FIG. 4D), and the clock tick routine (FIG. 4E).

The DOS subroutine is used by the main monitor routine return control to the operating system (i.e., to give the operating system 24 CPU cycles) when operating system 24 has polled the keyboard but no keyboard entries have been received. At block 131 the state of the monitor is saved on the monitor stack. Then, at block 132 the state of the operating system is retrieved from the DOS state, and (at block 133) the monitor "returns" (i.e., exits) to the operating system 24.

The SDOS subroutine is used by the match routine (see FIGS. 5A–5B) to send a keyboard entry to the operating system 24. If the operating system 24 is trying to poll the keyboard (see block 141) then the SDOS subroutine waits (see blocks 142 to 144) until the operating system tries to read the keyboard. It does this by (1) saving the value of KEYIN on the monitor stack (at block 142) for later use; (2) calling DOS (see FIG. 4A) with KEYIN as a parameter (at block 143), indicating that there has been a keyboard entry; and (3) retrieving KEYIN from the monitor stack (at block 144) when the operating system 24 restores control to the monitor 27 via a poll or read. This is done until DOS tries to read the keyboard.

When DOS 24 tries to read the keyboard, the main branch of the SDOS routine begins at block 145, where DOS 24 is called using KEYIN as a parameter. When DOS 24 restores control to the monitor 27 (via a poll or read), the monitor checks whether DOS is trying to do a poll or a read. If it is trying to do a poll the routine exits back to the monitor 27 at block 149. If DOS is trying to do a read, KEYIN is set to NULL (at block 147) and DOS is called with KEYIN as a parameter (at block 148). This tells DOS that there is nothing in the keyboard buffer for it to read. (The monitor does this even if there is something in the keyboard buffer because it has yet to determine if that data should be passed to DOS). When DOS returns control to the monitor the SDOS routine exits at block 149 back to the match routine.

Referring to FIG. 4B, the Keyboard Request Interrupt routine is invoked every time DOS 24 tries to poll or read the keyboard buffer. This is a software interrupt. The entry points of the poll and read routines are usually determined by items in a vector table set up by the operating system 24. These vectors can be changed by software to point to different poll and read routines than the routines originally designated by the operating system 24. The process of initializing the monitor (see block 41 in FIG. 3A) includes resetting these vectors to point to the Keyboard Request Interrupt routine.

The only tasks of the Keyboard Request Interrupt routine are to save the state of DOS on the DOS stack (block 151); retrieve the Monitor state from the monitor stack (block 153) and return (i.e., exit) to the monitor (block 154). However, the first time the monitor is called there is no monitor state to retrieve. Therefore the routine tests at block 151 whether this is the first time that DOS had done a poll or read since the vector table entries for keyboard request interrupts were changed. If it is, the monitor state is not retrieved from the monitor stack (i.e., block 153 is skipped) and the routine exits to the monitor (which effectively transfers the process to entry point A of the main monitor routine in FIG. 3A).

Referring to FIG. 4D, the Hardware Keyboard Interrupt routine responds when the student enters data into the system. It acts as a pre-amble to the standard system routine (herein GOROM) for handling keyboard entries. Normal data entries continue to be handled by the system's GOROM routine. Only certain special entries receive special handling. Four of these special entries are keystroke combinations that are normally illegal or not allowed by the operating system 24. The fifth special entry is any keystroke while the monitor is in the pause state.

If the monitor is in the "pause state" the normal flow of the monitor process continues except that the clock used for the timeout loop is frozen. In the program listings, below, the pause state is implemented in the MS_TICK routine by not incrementing the clock when the pause flag is set. Thus the system is not put into a "hard loop" when in the pause state. This allows system functions such as disk operations to continue even if the system appears to be in suspended animation. In effect the system is running at infinite speed (because no time is passing so far as the timeout clock is concerned) but appears to stopped to the casual outside observer.

Block 161 is the entry point of the keyboard interrupt routine. If the monitor 27 is in the pause state (block 161) any keyboard entry will terminate the pause state. This basically involves (see block 162) resetting the pause state flag, restoring the CRT (to the state it was in before the pause state was entered), and dismissing the interrupt (block 163). In the preferred embodiment, the keyboard entry used to exit the pause state is thrown away—it is not used as input to the system.

If the monitor 27 was not in the pause state, the routine checks to see if any of the special entries has been made. A HELP request entry ('CNTRL' 'SHIFT'), a REVIEW request entry ('CNTRL' 'TAB'), or a MENU request entry (detected at block 164, 166, or 168, respectively) causes the corresponding flag to be marked (at block 165, 167, or 169, respectively) for later use by the main monitor routine. After the flag is marked the interrupt is dismissed at block 163. In the entry was not a HELP, REVIEW, or MENU request then it is checked to see if it was a PAUSE request ('ALT''SPACE BAR') at block 171. If the entry is not a PAUSE request the system GOROM routine is called (block 172) to process the entry as a normal keyboard entry. If the entry is a PAUSE request, the character on the CRT screen at the current cursor position is saved (block 173) and replaced with a flashing capital "P" (block 174). The pause flag is marked (for use in the clock routine) at block 175 and the interrupt is dismissed. As will be understood by those skilled in the art, any visual reminder that the system is in a pause state is equivalent to the flashing "P" scheme just described.

Referring to FIG. 4E, the clock tick routine is a software interrupt routine that is invoked automatically every time the system clock "ticks" (e.g., every 18.2 microseconds in the preferred embodiment). In block 300 the routine checks whether the monitor 27 is in the pause state. If it is, then the routine does nothing and just return, via block 302. If the monitor is not in the pause state, then block 301 is executed. In the preferred embodiment, block 301 merely increments an internal counter called the master scheduler clock, which is used to determine when there is a timeout, as discussed above. In other embodiments, any monitor 27 or system function could be invoked from block 301. For instance, the monitor could be "returned" to under certain specified conditions (i.e., the DOS state would be saved and the monitor state retrieved from their respective stacks), much as though the operating system had performed a read. In another instance, the clock tick routine could periodically send a message to the system user or update a "clock" on one of the display devices.

Match Routine

Referring to FIGS. 5A and 5B, there is shown a flow chart of the match routine process. Whenever there is a "match" the next event pointer is set to the match event 74b (at block 211) specified by the branch which found the match. If a branch is tested and does not result in a match the process continues (at block 216) with next branch in the event, if there is one. If no match has been found and all the branches have been tested, the match routine exits (at block 218) back to the main monitor routine.

At block 181 the process is initiated by getting the pointer to the first branch from parameter 72d of the event structure. Block 182 begins the branch loop by getting the branch string 74f and branch flags. If the branch is a screen-match branch (i.e., if the BR_CRT_M flag is set) (see block 183) the CRT_MATCH routine is called (block 184). The CRT_MATCH routine determines whether the data on the CRT starting at the position indicated by the BR_X and BR_Y parameters 74d and 74e matches the branch string (also called the screen-match string). If it there is a match it sets the match flag (which is tested at block 187) and the process continues at entry point E to block 211 on FIG. 5B.

If the branch is not a screen-match branch the process checks the BR_OBJECT flag (at block 185) to see if it is an object branch. If the BR_OBJECT flag is set, then the branch is an object branch and the OBJEC- T_WORK routine is called (at block 186). See FIGS. 6A-6C for a flow chart of the OBJECT_WORK routine. If the object branch results in a "match" the process is directed by a decision block 187 to entry E to block 211. If no match results from the object branch the process is directed to block 216 on FIG. 5B.

If the branch is a match branch the process checks (at block 188) to see if any data entries have been received. If not, the process continues with the next branch (if any) at block 215 on FIG. 5B. If data has been received, the preferred embodiment processes the input in one of two ways.

If the BR_PASS flag is set (see decision block 189) the match string is a single wildcard character. See discussion above regarding wildcards. The wildcard routine (block 191) checks to see if the input data is within the set specified by the wildcard in the match string. If it is the match flag is set.

If the BR_PASS flag is not set, the match string can be any string of characters. The process at block 201 determines if the substring, including the previously entered data (entered since the character counter was last reset) and the last data entry, match the corresponding substring of the match string. If so there is a "submatch". (For example, if the match string is "PRINT" and the data entered so far is "PRI" there is a "submatch".)

The processing of wildcard and regular match branches is mostly the same after the check has been made for a wildcard match or a "submatch". At decision blocks 192 or 202, respectively, if there was no match or submatch the process continues at entry point D to block 216. If there was a wildcard match or submatch the BR_DOS flag is tested at block 193 or 203, respectively. If the BR_DOS flag is set, the last entry, which is in the KEYIN object, is passed to DOS by the SDOS routine at block 194 or 204, respectively. Next the BR_CRT flag is tested at block 195 or 205, respectively, and if it is set then the KEYIN character is sent to the CRT but not to DOS at block 196 or 206, respectively.

At this point the processing of wildcard and regular match branches diverges slightly. In the processing of regular match branches there is a test at block 207 to determine if the input data matches the whole match string or only a portion of it. If the only a portion of the match string has been matched the match flag is not set and the routine exits (at block 208) back to the main monitor routine. Otherwise the match flag is set (at block 209).

If there was a match, the next event pointer is set to the match event at block 211. If the BR_CALL flag is set (see decision block 212) the next event is marked as a call event (at block 213) and will be treated as the beginning of an event subroutine. If the BR_NOBR flag is not set (see decision block 214) the routine exits (at block 215) to the main monitor routine. If the BR_NOBR flag is set the match routine continues at block 216 as though no match had been found.

At block 216 the match routine prepares to test the next branch in the event, if there is one, by resetting the match flag, saving the KEYIN object (which holds the latest data entry) for use by the next branch and getting the pointer to the next branch. If the pointer is null (see decision block 217) there are no more branches and (at block 218) the KEYIN object is set to NULL and the routine exits back to the main monitor routine. If there are more branches, the match process resumes at entry point A to block 182 at the beginning of the branch loop.

Object Process

Figure 6B:
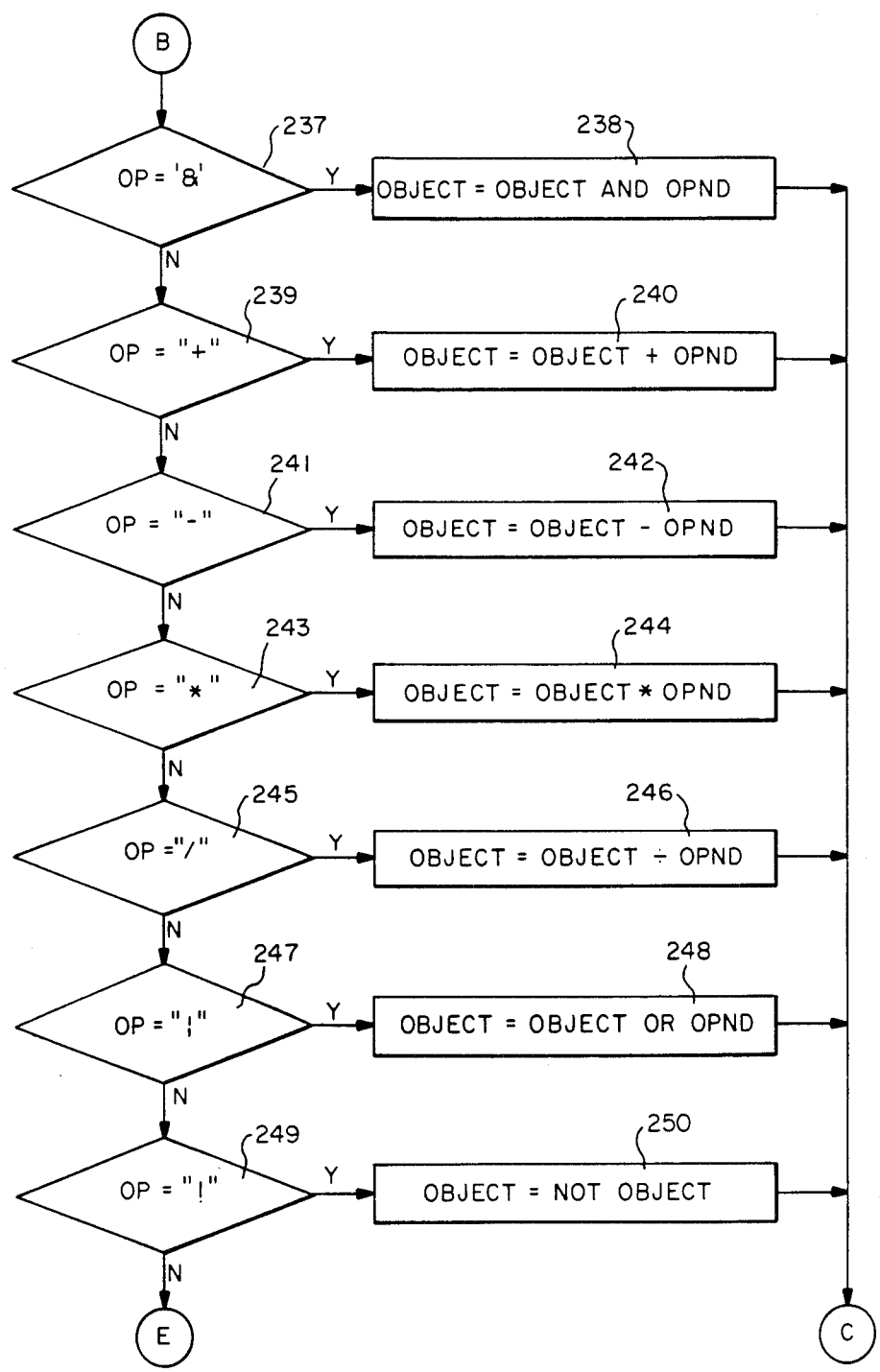

Referring to FIGS. 6A-6C, the OBJECT_WORK routine is basically a straightforward implementation of process for interpreting a string of characters representing one or more or the object operations shown in Table 4. As shown in Branch 3 of Table 1B, object operations are separated by semicolons.

Since two of the dedicated objects, CP and SHIFT, affect the physical state of the system the state of these system parameters are stored at the beginning of the object routine (at block 211) and are used to set the system state (at block 265) just before the object routine exits (at block 266).

The main object loop starts at block 222 where the object and the operator of the next object equation are read in and a string pointer is set to the next character in the branch string.

If there is an operand (note that not all object equations are operands), it is decoded and its effective value is put in a variable denoted OPND in the flow chart. There are three types of operands in the preferred embodiment; events, objects, and numbers. The types are distinguished by the value of the first byte of the operand: events and objects have unique prefixes not equal to any numerical operand. If the operand is an event (decision block 223) OPND equals the value of the event pointer to the event (block 224). If the operand is an object (decision block 225), the OPND equals the value of the object (block 226). If the operand is a number, the number is decoded (at block 227) as such. If there is no operand, OPND is equals zero.

Next, at block 228 the monitor advances the string pointer past any blanks at the end of the equation until it reaches either a semicolon or the end of the branch string. This merely prepares for checking at the end of the object loop to see if the monitor is done with the object branch.

In addition to changing the value of an object the object routine can either set (at block 262) or reset (at block 261) the match flag if a branch equation is performed.

In the odd numbered blocks from 231 to 255, the process checks to see what type of operator (OP) is used in the object equation. In the even numbered blocks from 232 to 256 the operation is performed if the corresponding operator was found. After mathematical and logical equations the process always continues at entry point C to block 261. After branch equations the process continues at entry point C to block 261 if the test was not satisfied and continues at entry point D to block 262 if the test was satisfied. The "@" operand always continues at entry point D since it is used only to force a branch. After video equations the process always continues at entry point C. (Note that in the program listings below routine at block 234 for the "V" operand is not implemented.)

If the process continues at block 261 (entry point C) the match flag is reset. If it continues at block 262 (entry point D) the match flag is set. Thus, when the object routine exits back to the main monitor routine the match flag is set only if the last object equation sets the match flag. The earlier object equations have no effect on the match flag as seen by the main monitor routine.

If all the object equations in the branch string have been processed (see decision block 263) then the shift state of the keyboard and the CRT cursor position are set in accordance with the current value of the SHIFT and CP objects (at block 265) and the object routine exits (at block 266) back to the main object routine. If the branch string contains more object equations the string pointer is advanced (at block 264) and the process continues at entry point A to block 222 at the beginning of the object loop.

Expert Systems

The current invention can be used as an expert system rather than a training system. By way of example, the invention can be used to supplement a medical diagnosis computer program. In such a system, the training/experts subsystem 30 interprets entered data in accordance with the context of the medical diagnosis computer program and provides additional visual information to the user, thereby facilitating the use of the expert system. It is anticipated that most expert systems using the invention will use the embodiment which incorporates a second display device, because the pictures provided by such a second display can greatly expand the power and usefulness of many expert system.

Furthermore, the invention's method of separating training/expert system tasks from the application's tasks, can be used to advantage in the design of new expert systems. Use of the invention will make possible the design of expert systems which would have been very difficult and cumbersome, if not impossible, using prior art techniques. For instance, an X-ray diagnosis expert system might contain an X-ray diagnosis computer program (i.e., an applications program) and courseware having a library of X-rays for display on the second display device and a set of corresponding events, coordinated with the computer program. Either the computer program and/or the courseware prompt the user of the system with questions relevant to analyzing X-rays. In response to the user's answers, different X-rays in the library are shown on the second display device. The goal of the expert system in this example is to maximize certain predefined indicia of similarity between the image displayed on the second display device and the X-ray that the user is trying to analyze. When the best match is found, the X-ray diagnosis computer program supplies the user with the diagnosis associated with the best-match X-ray shown on the second display device.

Courseware Authoring

The current invention does not include the process for authoring courseware. Given a specification for a software training program (for a particular target program 15), anyone skilled in the art could build the necessary data structures as shown in FIGS. 7A-7D.

While the present invention has been described with reference to a specific embodiment, the description is illustrative of the invention and is not to be construed as limiting the invention. Various modifications may occur to those skilled in the art without departing from the true spirit and scope of the invention as defined by the appended claims.

PROGRAM LISTINGS

The following program listings comprise one embodiment of the monitor module, data input interrupt and data request interrupt portions of the invention. All the programs, except for VID_WRK are written in standard assembler language for the IBM PC. VID_WRK is written in the C language. There are several texts available on the IBM PC assembler language and numerous tests on the C language. For ease of understanding the listings in this specification, the applicant refers to and incorporates as part of the disclosure, although not part of the invention, (1) a publication of International Business Machines, entitled IBM PC Hardware Reference Manual, copyrighted in 1982; and (2) a publication of Prentice Hall, entitled "the C Programming Language", copyrighted in 1978.

| Index to program listings: | |
|---|---|
| PROGRAM NAME | PROGRAM FUNCTION |
| MAIN | Main routine for monitor module |
| NXT_WRK | Point to next initial task |
| MATCH | Evaluate BRANCHES in an event |
| CRTM | Evaluate CRT match branches |
| OBJECT | Interpret an OBJECT string |
| "Utility" routines: | |
| GET_EVENT | Set up to use next event |
| DOS_STATE | Transfer control back to the operating system |
| SDOS | Send a specific character back to the operating system |
| KB_INT | Keyboard request interrupt routine - transfers control from operating system to training subsystem |
| HDW_KB | Keyboard interrupt routine |
| INIT_KB | Set keyboard interrupt vector to point to HDW_KB routine |
| INIT_DAT | Read in the event map and the event and the audio files. |
| Audio routines: | |
| INIT_AUD | Set up for audio |
| AUD_WRK | Play an audio message |
| Text routine: | |
| TXT_WRK | Send Text to the CRT, Printer or the operating system |
| Video routines: | |
| VID_WRK | Play a specified video image or sequence |
| Clock routines: | |
| MS_TICK | Time keeper for timeout loop |
| GETTICK | Get elapsed time value |
| INIT_MS | Set clock interrupt vector |
| START_TICK | Start clock for timeout loop |
| CHK_TICK | Check for timeout |
| WAIT | Kill time until end of pause |

What is claimed is:

1. An interactive training system for training a person to use a preselected computer program, comprising:
 (a) a computer subsystem including
  CPU means for executing computer programs,
  input means for entering data into said system, and
  display means for displaying the results of executing a computer program in said CPU;
 (b) means for loading said preselected computer program in said computer subsystem; and
 (c) tutor means comprising a second distinct computer program resident in said computer subsystem for training said person to use said preselected computer program while said computer subsystem runs said preselected computer program, wherein said second distinct computer program operates as a coroutine to said preselected computer program, said tutor means including:
  a courseware database for defining a tutorial for training a person to use said preselected computer program, including data structures for defining, in accordance with the contextual circumstances in the running of said preselected computer program, (a) criteria for determining whether said input data is to be processed by said preselected computer program, and (b) tutorial messages to be displayed on said display means in response to said input data;

interrupt means for interrupting the flow of data from said input means to said preselected computer program so that said input data can be compared with said courseware database criteria, monitor means for interpreting and manipulating said input data, selectively generating tutorial messages in reponse to said input data, and selectively allowing a subset of said input data to be processed by said preselected computer program; said interpreting, manipulating, generating and allowing functions being dynamically determined in accordance with predefined criteria in said courseware database dependent on the contextual circumstances in the running of said preselected computer program, and display control means for separately displaying said tutorial messages and the output from said preselected computer program so that said person can distinguish tutorial messages from normal output from said preselected computer program;

wherein the content and flow of said tutorial is defined by said data structures in said courseware database.

2. A system as set forth in claim 1, wherein
said courseware database includes data structures for defining a plurality of events, each event corresponding to one or more contextual circumstances in the running of said selected computer program, each said event defining one or more tasks to be performed, wherein the performance of a plurality of said tasks is conditional upon predefined criteria and the content of said input data;

said monitor means includes means for dynamically selecting one of said events, in accordance with the contextual circumstances in the running of said preselected computer program, for use in determining the criteria to be used in the performance of said interpreting, manipulating, generating and allowing functions; and said interrupt means includes means for transferring control of said CPU means to said monitor means before said input data is processed by said preselected computer program.

3. A system as set forth in claim 2, wherein
said computer subsystem further includes operating system means for providing an environment for the running of applications programs; and said interrupt means includes means for transferring control to said monitor means upon the occurrence of a poll or read by a program in said CPU means.

4. A system as set forth in claim 3, wherein
a plurality of said events define explanational messages to be generated when said input data does not match any one of a predefined set of one or more match values corresponding to valid data entries in the context corresponding to said event.

5. A system as set forth in claim 2, wherein said display means includes first and second display elements; said first display element being used for displaying images defined by said preselected computer program; and said second display element being used for displaying images defined by said courseware database;

whereby visual explanational messages can be displayed simultaneously with the display of images generated by said preselected computer program.

6. A system as set forth in claim 5, wherein
said first and second display elements comprise windows within a single monitor display; and said monitor means includes means for windowing the display of said display means and for displaying explanational messages in at least one window on said display.

7. A system as set forth in claim 5, wherein said first and second display elements each comprises a separate displays means;

wherein a plurality of said events further include means for specifying images to be displayed on said second display element;

whereby explanational messages can be displayed on said second display element without affecting the display of the first display element.

8. A system as set forth in claim 7, wherein
a plurality of events further include a set of one or more initial tasks to be performed when said event is invoked by said monitor means; a plurality of said initial tasks causing the display of predefined images on said second display means.

9. A system as set forth in claim 7, wherein
said second display means includes laser disk means for displaying one or more frames of pictures in sequence;

whereby said visual explanational messages can include pictures of the computer system, or portions thereof, being used by said student and can particularly point out the next action to be taken by the student.

10. A system as set forth in claim 2, wherein
a plurality of said events define one or more match values and also define a set of one or more tasks corresponding to each match value, said sets of tasks to be performed by said monitor means upon the receipt of input data which matches the match value corresponding to said sets of tasks; and said monitor means includes means for comparing said input data with one or more predefined match values in a selected event, and for performing the corresponding predefined tasks upon the occurrence of a match;

wherein a plurality of said tasks allow said input data to be processed by said preselected computer program; a plurality of said tasks cause said monitor means to select a specified event as the event to be used in conjunction with the next input datum; and a plurality of said tasks cause the generation of an explanational message; and wherein a plurality of said sets of tasks do not allow said input data to be processed by said preselected computer program.

11. A system as set forth in claim 10, wherein
said courseware includes means for defining for each of a plurality of said events a timeout parameter corresponding to the maximum amount of time the system should wait for input data which matches a match value defined by said event before invoking a predefined timeout event, and for defining a timeout event to be invoked upon timeout; and said monitor means includes timer means for repetitively comparing the amount of elapsed time since a first defined time with said timeout parameter, and for invoking said timeout event upon timeout.

12. A system as set forth in claim 2, wherein
said courseware includes means for defining, for each of a plurality of events, a set of one or more branches;
a plurality of said branches define a match value and a set of one or more corresponding tasks to be performed upon the occurrence of a match between said input data and said match value;
a plurality of said branches define a screen match value and a set of one or more corresponding tasks to be performed upon the occurrence of a match between said screen match value and a specified portion of the display associated with said display means; and
said monitor means includes means for testing said branches in a selected event and for performing said corresponding tasks upon the occurrence of a match.

13. A system as set forth in claim 12, wherein
a plurality of said events include a loop flag; and said monitor means includes means, responsive to the presence of said loop flag in a selected event, for repetitively testing those branches in said selected event which define a screen match value, regardless of the receipt of input data.

14. A system as set forth in claim 13, wherein
a plurality of said events include means for defining a maximum allowable amount of input data to be received before a match is found by said monitor means;
said monitor means includes means for invoking a specified event if the amount of input data received exceeds said maximum allowable amount;
whereby a student can be allowed to make a plurality but limited number of entries until said preselected computer program produces a display, a predefined portion of which matches a predefined screen match value.

15. A system as set forth in claim 12, wherein
said courseware includes a plurality of distinct wildcard means, each defining a match value which encompasses a predefined set of data input values;
whereby certain classes of input data can be processed by said monitor means on the basis of the class of data received rather than the specific value of the data received.

16. A system as set forth in claim 12, wherein
a plurality of said branches are object branches, each said object branch defining one or more object operations on objects, each object comprising a variable quantity and a plurality of said object operations comprising a mathematical or comparative operation.

17. A system as set forth in claim 16, wherein
said objects include an object for defining a menu event, and an object for defining a help event;
said monitor means includes means for responding to a first predefined input data value by invoking said menu event, and means for responding to a second predefined input data value by invoking said help event;
at least one of said object branches includes means for specifying the current value of said menu event, and at least one of said object branches includes means for specifying the current value of said help event.

18. A system as set forth in claim 12, wherein
said courseware includes flag means for specifying for each of a plurality of events whether to test at least certain ones of the branches in said event before testing for timeout;
said monitor means includes means responsive to said flag means for executing at least certain ones of the branches in a selected event before testing for timeout.

19. In a method of controlling a computer system to train a person to use a preselected computer program while said computer subsystem runs said preselected computer program,
said computer system having a computer subsystem including CPU means for executing computer programs, input means for entering data into said system and display means for displaying the results of executing a computer program in said CPU;
the steps comprising:
loading and running said preselected computer program;
loading into said computer subsystem a courseware database for defining a training program for training a person to use said preselected computer program, said courseware including data structures for defining, in accordance with a plurality of contextual circumstances in the running of said preselected computer program, (a) criteria for determining whether said input data is to be processed by said preselected computer program, and (b) tutorial messages to be displayed on said display means in response to said input data; and
concurrently, while running said preselected computer program, performing a monitor coroutine including the steps of:
interrupting the flow of input data from said input means to said preselected computer program;
interpreting said input data;
selectively generating tutorial messages in response to said input data; and
selectively allowing a subset of said input data to be processed by said selected computer program; and
displaying the output from said preselected computer program separately from said tutorial messages so that said person can distinguish tutorial messages from normal output from said preselected computer program;
said interpreting, generating and allowing steps being performed in accordance with said criteria defined by said courseware.

20. A method as set forth in claim 19, wherein
said courseware includes a database formatted in accordance with a predefined data structure or set of data structures for defining a plurality of events, each event corresponding to one or more contextual circumstances in the running of said preselected computer program, each said event defining one or more tasks to be performed, wherein the performance of a plurality of said tasks is conditional upon predefined criteria and the content of said input data;
said interpreting step includes dynamically selecting one of said events, in accordance with the contextual circumstances in the running of said preselected computer program, for use in determining the criteria to be used in the performance of said interpreting, generating and allowing steps; and said interrupt step includes invoking said interpreting step before said input data is processed by said preselected computer program.

21. A method as set forth in claim 20, wherein
a plurality of said events specify a set of one or more initial tasks to be performed when said event is selected.

22. A method as set forth in claim 20, wherein said interpreting step includes:
responding to the failure of the system to receive data that matches a specified match value within a predefined timeout period of time, defined in accordance with the event being used to interpret said data, by invoking a predefined timeout event.

23. A method as set forth in claim 20, wherein
said courseware defines, for each of a plurality of events, a set of one or more branches;
a plurality of said branches define a match value and a set of one or more corresponding tasks to be performed upon the occurrence of a match between said input data and said match value;
a plurality of said branches define a screen match value and a set of one or more corresponding tasks to be performed upon the occurrence of a match between said screen match value and a specified portion of the display associated with said display means; and
said interpreting step includes testing said branches in a selected event, and said interpreting, generating and allowing steps include performing said corresponding tasks upon the occurrence of a match.

24. A method as set forth in claim 23, wherein said interrupting step includes responding to poll and read requests by said preselected computer program by initiating said interpreting step.

* * * * *